US009625365B2

(12) United States Patent
Ho et al.

(10) Patent No.: US 9,625,365 B2
(45) Date of Patent: Apr. 18, 2017

(54) SYSTEM AND METHOD FOR MONITORING PARTICLES IN SOLUTION

(71) Applicant: Industrial Technology Research Institute, Hsinchu (TW)

(72) Inventors: Hsin-Chia Ho, Hsinchu County (TW); Guo-Dung Chen, New Taipei (TW); Wei-En Fu, Taoyuan (TW); Yen-Liang Lin, Taichung (TW)

(73) Assignee: Industrial Technology Research Institute, Hsinchu, Taiwan (TW)

( * ) Notice: Subject to any disclaimer, the term of this patent is extended or adjusted under 35 U.S.C. 154(b) by 0 days.

(21) Appl. No.: 14/631,861

(22) Filed: Feb. 26, 2015

(65) Prior Publication Data

US 2015/0330886 A1 Nov. 19, 2015

(30) Foreign Application Priority Data

May 16, 2014 (TW) .............................. 103117381 A
Nov. 4, 2014 (TW) .............................. 103138188 A

(51) Int. Cl.
*G01N 15/02* (2006.01)
*G01N 15/10* (2006.01)
(Continued)

(52) U.S. Cl.
CPC ..... *G01N 15/0266* (2013.01); *B01F 3/04056* (2013.01); *B01F 5/0609* (2013.01);
(Continued)

(58) Field of Classification Search
CPC .......... B01F 2215/0037; B01F 3/04056; B01F 11/0071; B01F 15/0238; B01F 5/0609;
(Continued)

(56) References Cited

U.S. PATENT DOCUMENTS 5,007,297 A 4/1991 Sommer
5,098,657 A * 3/1992 Blackford .......... G01N 15/0656
239/74

(Continued)

FOREIGN PATENT DOCUMENTS

CN 100374189 3/2008
CN 102500559 6/2012
(Continued)

OTHER PUBLICATIONS

Mulholland et al., "Measurement of 100 nm and 60 nm Particle Standards by Differential Mobility Analysis," Journal of Research of the National Institute of Standards and Technology, Jul.-Aug. 2006, pp. 257-312.

(Continued)

*Primary Examiner* — Tri T Ton
(74) *Attorney, Agent, or Firm* — Jianq Chyun IP Office

(57) ABSTRACT

An apparatus for mixing a solution includes first and second tanks, a sampling element, a flow control element, a mixing assembly, first and second air-intake systems, and first and second air-exhaust systems. The first tank has a first chamber. The second tank has a second chamber. The sampling element has an extraction port located in the first chamber. The flow control element connects and communicates with the first chamber. Two opposite ends of the mixing assembly connect and communicate with the first chamber and the second chamber, respectively. The first air-intake system and the first air-exhaust system connect and communicate with the first chamber. The second air-intake system and the second air-exhaust system connect and communicate with the second chamber.

19 Claims, 15 Drawing Sheets

(51) Int. Cl.

| | | |
|---|---|---|
| *B01F 3/04* | (2006.01) | |
| *B01F 5/06* | (2006.01) | |
| *B01F 11/00* | (2006.01) | |
| *B01F 15/02* | (2006.01) | |
| *G01N 1/28* | (2006.01) | |
| *G01N 1/38* | (2006.01) | |
| *G01N 15/00* | (2006.01) | |

(52) U.S. Cl.
CPC ...... *B01F 11/0071* (2013.01); *B01F 15/0238* (2013.01); *G01N 1/28* (2013.01); *G01N 1/38* (2013.01); *G01N 15/0205* (2013.01); *G01N 15/10* (2013.01); *B01F 2215/0037* (2013.01); *G01N 2015/0038* (2013.01); *G01N 2015/1081* (2013.01); *G01N 2015/1087* (2013.01)

(58) Field of Classification Search
CPC ............... G01N 15/0205; G01N 15/10; G01N 2015/1081; G01N 2015/1087; G01N 15/0266; G01N 1/28; G01N 1/38; G01N 2015/0038
USPC .................................................. 356/335–343
See application file for complete search history.

(56) References Cited

U.S. PATENT DOCUMENTS

| | | | |
|---|---|---|---|
| 6,211,956 B1 * | 4/2001 | Nicoli | G01N 15/02 356/337 |
| 6,263,744 B1 | 7/2001 | Russell et al. | |
| 6,639,671 B1 * | 10/2003 | Liu | G01N 15/0205 250/574 |
| 6,923,568 B2 | 8/2005 | Wilmer et al. | |
| 7,213,476 B2 | 5/2007 | Cheng et al. | |
| 7,259,018 B2 | 8/2007 | Benner et al. | |
| 7,298,486 B2 | 11/2007 | Wang et al. | |
| 7,576,319 B2 | 8/2009 | Miller et al. | |
| 7,777,868 B2 | 8/2010 | Blackford et al. | |
| 7,851,224 B2 | 12/2010 | Benner et al. | |
| 8,097,462 B2 | 1/2012 | Benner et al. | |
| 8,186,733 B2 | 5/2012 | Geary et al. | |
| 8,272,253 B2 | 9/2012 | Grant et al. | |
| 8,297,830 B2 | 10/2012 | Tseng et al. | |
| 8,524,482 B1 | 9/2013 | Wick | |
| 8,573,034 B2 | 11/2013 | Grant et al. | |
| 8,698,076 B2 * | 4/2014 | Orii | G01N 15/0266 250/288 |
| 9,086,350 B2 | 7/2015 | Grant et al. | |
| 2010/0209628 A1 | 8/2010 | Girshick et al. | |
| 2012/0312084 A1 | 12/2012 | Grant et al. | |
| 2013/0236396 A1 | 9/2013 | Pease, III et al. | |

FOREIGN PATENT DOCUMENTS

| | | |
|---|---|---|
| CN | 102620959 | 8/2012 |
| TW | 273009 | 3/1996 |
| TW | 523824 | 3/2003 |
| TW | I286084 | 9/2007 |
| TW | 200916183 | 4/2009 |
| TW | 200940436 | 10/2009 |
| TW | I319085 | 1/2010 |
| TW | I382465 | 1/2013 |
| TW | M452036 | 5/2013 |

OTHER PUBLICATIONS

Eichler et al., "Improvement of the Resolution of TSI's 3071 DMA via Redesigned Sheath Air and Aerosol Inlets," Aerosol Science and Technology, Jul. 1998, pp. 39-49.
Moisala et al., "On-line detection of single-walled carbon nanotube formation during aerosol synthesis methods," Carbon, May 2005, pp. 2066-2074.
Kim et al., "In-Flight Kinetic Measurements of the Aerosol Growth of Carbon Nanotubes by Electrical Mobility Classification," J. Phys. Chem. B, Feb. 2006, pp. 4555-4562.
Lenggoro et al., "Sizing of Colloidal Nanoparticles by Electrospray and Differential Mobility Analyzer Methods," Langmuir, May 2002, pp. 4584-4591.
Kim et al., "Slurry Abrasive Particle Size Measurement by Scanning Mobility Particle Sizer," International Conference on Planarizaiton/CMP Technology, Nov. 19-21, 2009, pp. 60-64.
Bacher et al., "Charge-reduced nano electrospray ionization combined with differential mobility analysis of peptides, proteins, glycoproteins, noncovalent protein complexes and viruses," Journal of Mass Spectrometry, Sep. 2001, pp. 1038-1052.
Henderson et al., "The Optimum Particle-Size Distribution of Coal for Coal-Water Slurries," Atlantic Rsearch Corporation, 1987, pp. 1-11.
Intra et al., "An overview of differential mobility analyzers for size classification of nanometer-sized aerosol particles," Songklanakarin J. Sci. Technol., Mar.-Apr. 2008, pp. 243-256.
Krebs et al., "Two-dimensional alignment of differential mobility spectrometer data," Sensors and Actuators B, Dec. 7, 2006, pp. 475-482.
Sakurai et al., Abstract of "Distinctive Detection of Airborne Engineered Nanoparticles by On-line Aerosol Measurement Techniques," American Association for Aerosol Research 28th Annual Conference, Apr. 22, 2009, pp. 1.
Giechaskiel et al., "Calibration of Condensation Particle Counters for Legislated Vehicle Number Emission Measurements," Aerosol Science and Technology, Oct. 5, 2009, pp. 1164-1173.

* cited by examiner

FIG. 11

SYSTEM AND METHOD FOR MONITORING PARTICLES IN SOLUTION

CROSS-REFERENCE TO RELATED APPLICATION

This application claims the priority benefits of Taiwan application serial no. 103117381, filed on May 16, 2014, and Taiwan application serial no. 103138188, filed on Nov. 4, 2014. The entirety of each of the above-mentioned patent applications is hereby incorporated by reference herein and made a part of specification.

TECHNICAL FIELD

The disclosure relates to an apparatus and a method for mixing a solution and a system and a method for monitoring particles in a solution.

BACKGROUND

With the development of integrated circuits toward high density and high performance, the reduction of line width requires a light source with the reduced wavelength. Under said circumstances, the planarity of the wafer surface and the cleanness of a wet process are both relevant to the manufacturing yield. If the chemical mechanical polishing technique is applied for planarization, the polishing agent used in the technique is the factor of the polishing quality, and thus the quality control lies in the management of the size distribution of the particles in the polishing agent. In addition, particles and impurities in the solutions (e.g., hydrogen peroxide, a photoresist cleansing solution, ammonia, a developer, and so on) applied in various wet processes also pose an impact on the manufacturing yield and thus call for the attention from semiconductor manufacturers. In order to control quality through 24-hour online monitoring of the size distribution of the particles in a solution, a 24-hour automatic sampling and mixing apparatus has been developed. Given the fixed dilution rate and the even mixture, the relative concentration of the monitored solution can serve as the basis of quality control.

In general, the polishing agent may be mixed with a dilution agent for adjusting its concentration. However, the particles in the mechanically stirred polishing agent may aggregate or fall off, and therefore the use of mechanical mixing equipment (e.g., a stirring magnet or a cyclic pump) for stirring the solution may be prohibited. The mixing effects achieved by a non-mechanical static mixer are proportional to the effective mixing length; the greater the length of the static mixer, the better the mixing effects achieved. The increase in the length of the mixing equipment, however, also leads to the increase in the space occupied, and therefore it is rather unfavorable to integrate multiple non-mechanical mixing equipments into a miniaturized machine.

At present, the common tools for particle size inspection include a particle size analyzer and a liquid particle counter which are capable of monitoring the size distribution of particles in a liquid solution or monitoring the number of particles in the solution, and the minimum detectable size of the particles may reach 40 nm-200 nm. The widely-applied line width in the existing semiconductor manufacturing process is at most 28 nm, and thus neither the resolution of the particle size analyzer nor the resolution of the liquid particle counter can satisfy the industrial requirement for online monitoring of the nano-scale particles in the solution.

SUMMARY

According to an embodiment of the disclosure, a system for monitoring particles in a solution includes a solution mixing apparatus and an analysis equipment. The solution mixing apparatus is configured to extract a first solution with a fixed volume as well as dilute and mix the first solution at a predetermined ratio to form a sample solution. The analysis equipment is connected to the solution mixing apparatus and includes an aerosolization apparatus, a particle size classifier, and a particle counter. The aerosolization apparatus is configured to receive the sample solution and aerosolize the sample solution into a plurality of aerosolized particles. The particle size classifier is connected to the aerosolization apparatus and configured to receive the aerosolized particles and classify the aerosolized particles whose sizes fall within a designated range. The particle counter is connected to the particle size classifier and configured to receive the classified aerosolized particles and calculate the number of the classified aerosolized particles.

According to an embodiment of the disclosure, a method for monitoring particles in a solution includes but is not limited to following steps. A first solution is introduced into a solution mixing apparatus, and the first solution with a fixed volume is extracted by the sampling apparatus. The first solution is diluted and mixed at a predetermined ratio by the solution mixing apparatus to form a sample solution. The sample solution is aerosolized into a plurality of aerosolized particles by an aerosolization apparatus. The aerosolized particles whose sizes fall within a designated range are classified by a particle size classifier. The number of the classified aerosolized particles is calculated by a particle counter.

If the first solution does not require the pre-treatment, e.g., dilution and mixture, said sampling step and pre-treatment may be omitted; instead, the sample solution is introduced into the aerosolization apparatus to form the aerosolized particles, and subsequent steps may then be performed.

According to an embodiment of the disclosure, an apparatus for mixing a solution includes a first tank, a second tank, a sampling element, a flow control element, a mixing assembly, a first air-intake system, a first air-exhaust system, a second air-intake system, and a second air-exhaust system. The first tank includes a first chamber, a first fluid inlet, a first air-intake port, and a first air-exhaust port. The first fluid inlet, the first air-intake port, and the first air-exhaust port respectively connect and communicate with the first chamber. The second tank includes a second chamber, a second air-intake port, and a second air-exhaust port. The second air-intake port and the second air-exhaust port respectively connect and communicate with the second chamber. The sampling element has an extraction port that is located in the first chamber. The flow control element connects and communicates with the first chamber through the first fluid inlet. One end of the mixing assembly connects and communicates with the first chamber, and the other end of the mixing assembly opposite to the one end connects and communicates with the second chamber. The first air-intake system and the first air-exhaust system respectively connect and communicate with the first chamber through the first air-intake port and the first air-exhaust port. The second air-intake system and the second air-exhaust system respectively connect and communicate with the second chamber through the second air-intake port and the second air-exhaust port.

According to an embodiment of the disclosure, a method for mixing the solution includes but is not limited to following steps. A first solution is infused into a first chamber. The first solution is extracted from the first chamber by a sampling element, and an extraction amount of the first solution is controlled. The first solution in the first chamber is cleaned out. The first solution extracted by the sampling element is re-infused into the first chamber. A second solution is infused into the first chamber, and an infusion amount of the second solution is controlled by a flow control element. The first solution and the second solution are enabled to repeatedly flow through a mixing assembly between the first chamber and the second chamber by a pressure difference between the first chamber and the second chamber, and the pressure difference is generated by a first air-intake system, a first air-exhaust system, a second air-intake system, and a second air-exhaust system.

Several exemplary embodiments accompanied with figures are described in detail below to further describe the disclosure in details.

BRIEF DESCRIPTION OF THE DRAWINGS

Figure 11:
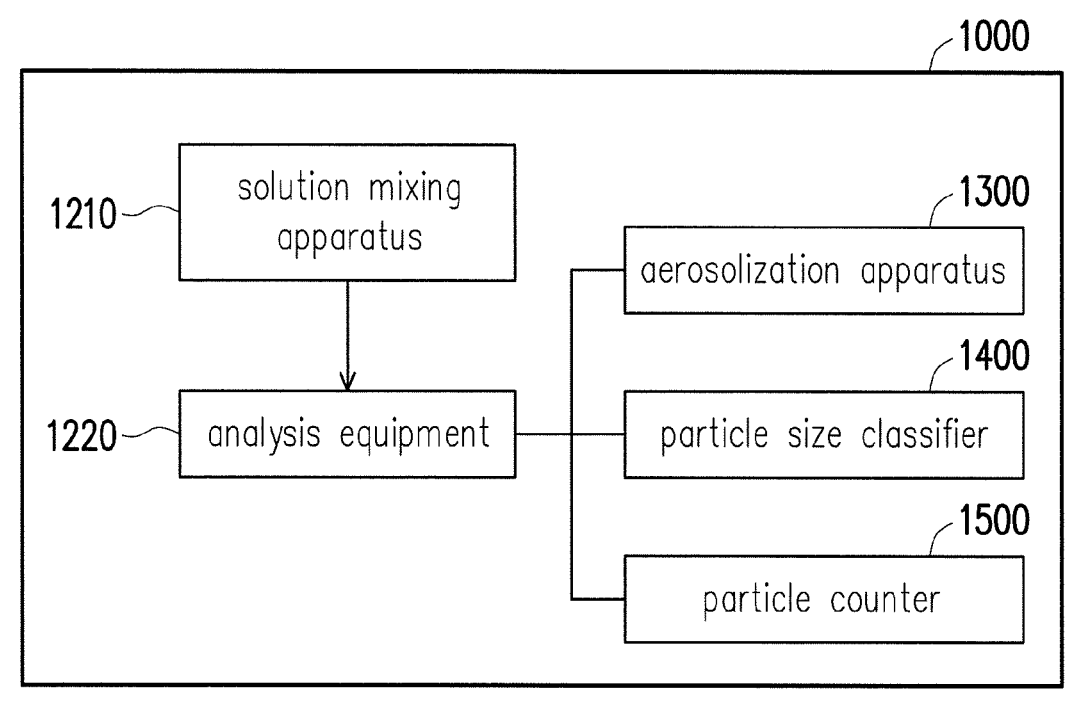

FIG. 11 is a schematic diagram illustrating an apparatus for monitoring particles in a solution according to an embodiment of the disclosure.

DETAILED DESCRIPTION OF DISCLOSED EMBODIMENTS

Figure 1:
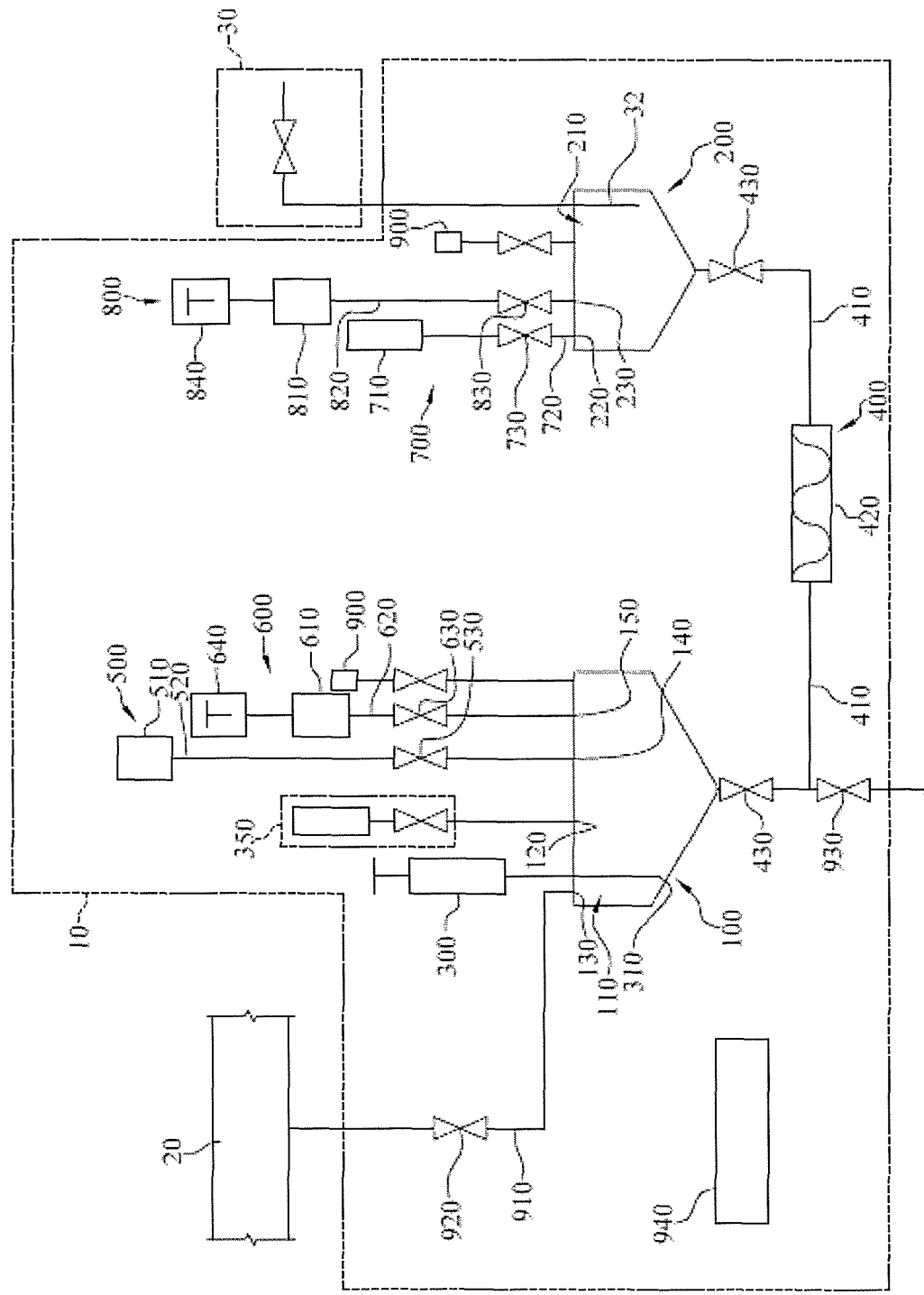
FIG. 1 is a schematic systematic diagram illustrating a solution mixing apparatus connected to a pipeline and analysis equipment according to an embodiment of the disclosure.

FIG. 1 is a schematic systematic diagram illustrating a solution mixing apparatus connected to a pipeline and analysis equipment according to an embodiment of the disclosure.

In the present embodiment, the solution mixing apparatus 10 includes a first tank 100, a second tank 200, a sampling element 300, a flow control element 350, a mixing assembly 400, a first air-intake system 500, a first air-exhaust system 600, a second air-intake system 700, and a second air-exhaust system 800.

The first tank 100 includes a first chamber 110, a first fluid inlet 120, a second fluid inlet 130, a first air-intake port 140, and a first air-exhaust port 150. The first fluid inlet 120, the second fluid inlet 130, the first air-intake port 140, and the first air-exhaust port 150 may respectively connect and communicate with the first chamber 110.

Figure 2:
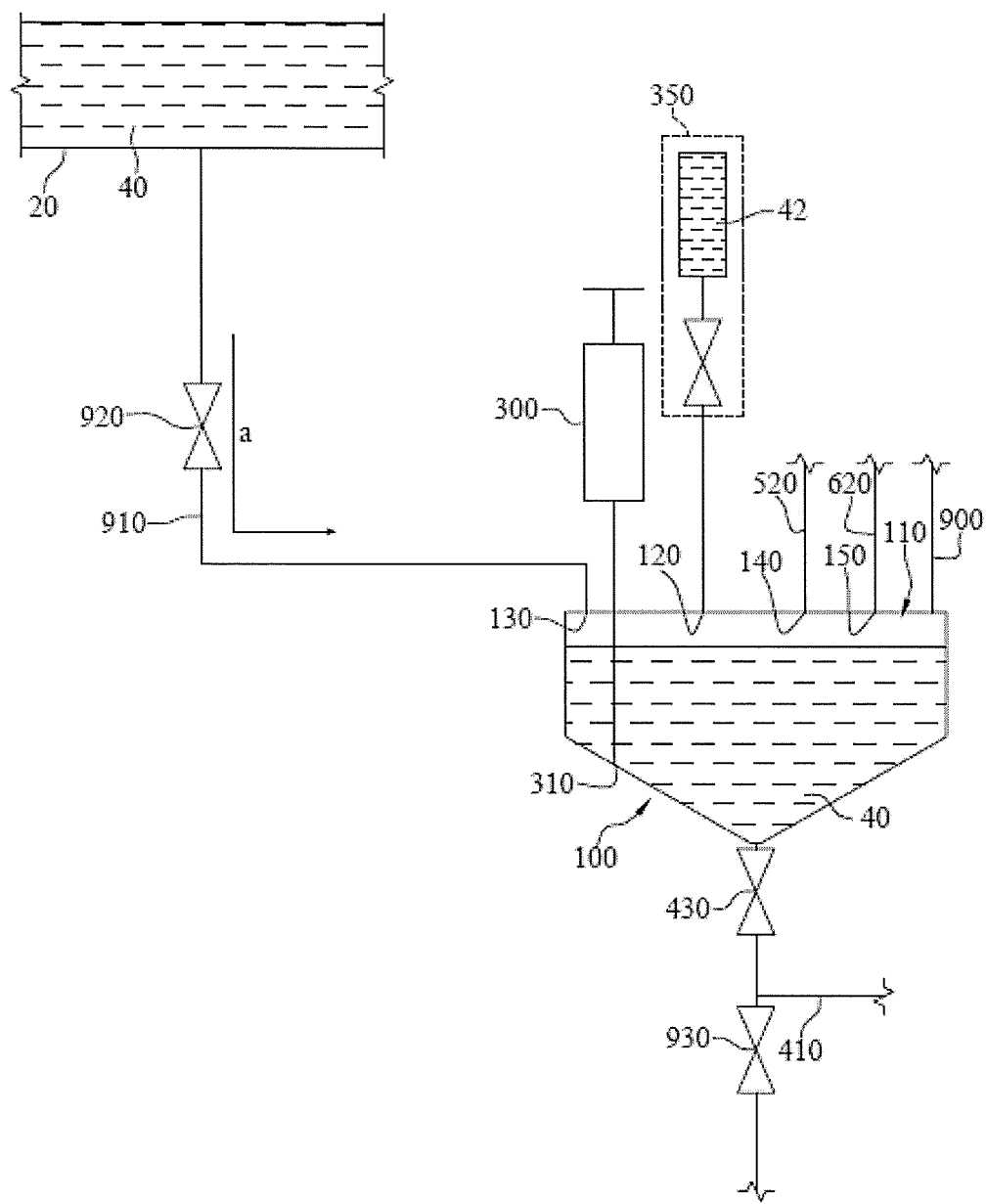
FIG. 2 is a schematic planar diagram illustrating that a first solution in a pipeline is infused into a first chamber through a second fluid inlet.

The solution mixing apparatus 10 may further include a first conduit 910 and a first switch valve 920. Two opposite ends of the first conduit 910 are respectively connected to the second fluid inlet 130 and a pipeline 20. A first solution 40 (as shown in FIG. 2) may be arranged in the pipeline 20, and the first solution 40 is, for instance, a chemical solution (e.g., slurry) applicable in a semiconductor manufacturing process. The first switch valve 920 may be arranged on the first conduit 910 for enabling or disabling the flow into or out of the first conduit 910.

The second tank 200 includes a second chamber 210, a second air-intake port 220, and a second air-exhaust port 230. The second air-intake port 220 and the second air-exhaust port 230 may respectively connect and communicate with the second chamber 210. The second chamber 210 may further connect and communicate with analysis equipment 30. Specifically, the analysis equipment 30 has a sampling end 32 that is located in the second chamber 210. Here, the analysis equipment 30 may be replaced by an aerosolization particle size analyzer or an aerosolization apparatus 1300, a particle size classifier 1400, and a particle counter 1500 in a monitoring apparatus provided hereinafter.

The sampling element 300 is, for instance, a syringe pump, a peristaltic pump, or a sample loop with a pump, and the sampling element 300 has an extraction port 310. The sampling element 300 passes through the first tank 100, and the extraction port 310 is located in the first chamber 110.

The flow control element 350 connects and communicates with the first chamber 110 through the first fluid inlet 120. The flow control element 350 serves to control a total flow mass of a second solution 42 (shown in FIG. 2) flowing into the first chamber 110. The second solution 42 is a diluted solution, e.g., de-ionized water.

One end of the mixing assembly 400 connects and communicates with the first chamber 110, and the other end of the mixing assembly 400 opposite to the one end connects and communicates with the second chamber 210. The mixing assembly 400 may include at least two second conduits 410 and a mixer 420. The two second conduits 410 respectively connect and communicate with two opposite ends of the mixer 420, and the two second conduits 410 respectively connect and communicate with the first chamber 110 and the second chamber 210. The mixer 420 provided in the present embodiment may be a static mixer. Inside the static mixer, there may be a stationary fan-shaped structure or any other structure capable of generating eddy flows; through guidance by said structure, fluids flowing through the mixer may be converted into the eddy flows, so as to achieve the mixing effects.

In an embodiment of the disclosure, the mixing assembly 400 may further include two second switch valves 430. The two second switch valves 430 are respectively arranged on the two second conduits 410 for enabling or disabling the flow into or out of the two second conduits 410, respectively.

The first air-intake system 500 and the first air-exhaust system 600 may respectively connect and communicate with the first chamber 110 through the first air-intake port 140 and the first air-exhaust port 150, so as to control the air pressure in the first chamber 110. To be specific, the first air-intake system 500 may further include first air-intake equipment 510, a first air-intake conduit 520, and a first air-intake valve 530. Two opposite ends of the air-intake conduit 520 respectively connect and communicate with the first air-intake port 140 and the first air-intake equipment 510. The first air-intake valve 530 is arranged on the first air-intake conduit 520 for enabling or disabling the flow into the first air-intake conduit 520. When the first air-intake valve 530 is open, the first air-intake equipment 510 may introduce air into the first chamber 110, so as to add the air pressure in the first chamber 110. The air introduced by the first air-intake equipment 510 may be compressed air, nitrogen, or an inert gas, for instance.

The first air-exhaust system 600 may further include first air-exhaust equipment 610, a first air-exhaust conduit 620, and a first air-exhaust valve 630. Two opposite ends of the first air-exhaust conduit 620 respectively connect and communicate with the first air-exhaust port 150 and the first air-exhaust equipment 610. The first air-exhaust valve 630 is arranged on the first air-exhaust conduit 620 for enabling or disabling the flow out of the first air-exhaust conduit 620. When the first air-exhaust valve 630 is open, the first air-exhaust equipment 610 may exhaust air from the first chamber 110, so as to lower the air pressure in the first chamber 110. In an embodiment of the disclosure, the first air-exhaust system 600 may further include a first reflow element 640 that connects and communicates with the first air-exhaust conduit 620.

The second air-intake system 700 and the second air-exhaust system 800 may respectively connect and communicate with the second chamber 210 through the second air-intake port 220 and the second air-exhaust port 230, so as to control the air pressure in the second chamber 210.

According to an embodiment of the disclosure, the second air-intake system 700 may further include second air-intake equipment 710, a second air-intake conduit 720, and a second air-intake valve 730. Two opposite ends of the second air-intake conduit 720 respectively connect and communicate with the second air-intake port 220 and the second air-intake equipment 710. The second air-intake valve 730 is arranged on the second air-intake conduit 720 for enabling or disabling the flow into the second air-intake conduit 720. When the second air-intake valve 730 is open, the second air-intake equipment 710 may introduce air into the second chamber 210, so as to add the air pressure in the second chamber 210. The air introduced by the second air-intake equipment 710 may be compressed air, nitrogen, or an inert gas, for instance.

The second air-exhaust system 800 may further include second air-exhaust equipment 810, a second air-exhaust conduit 820, and a second air-exhaust valve 830. Two opposite ends of the second air-exhaust conduit 820 respectively connect and communicate with the second air-exhaust port 230 and the second air-exhaust equipment 810, and the second air-exhaust valve 830 is arranged on the second air-exhaust conduit 820 for enabling or disabling the flow out of the second air-exhaust conduit 820. When the second air-exhaust valve 830 is open, the second air-exhaust equipment 810 may exhaust air from the second chamber 210, so as to lower the air pressure in the second chamber 210. In an embodiment of the disclosure, the second air-exhaust system 800 may further include a second reflow element 840 that connects and communicates with the second air-exhaust conduit 820.

In an embodiment of the disclosure, the solution mixing apparatus 10 may further include a drain switch valve 930. The drain switch valve 930 is arranged on the second conduit 410 between the first tank 100 and the mixer 420. However, the disclosure is not limited thereto, and the drain switch valve 930 can be arranged on the bottom of the first tank 100 or the second tank 200, so as to drain fluids from the first chamber 110 or the second chamber 210.

In an embodiment of the disclosure, the solution mixing apparatus 10 may further include cleansing equipment 900. The cleansing equipment 900 may be connected to the first tank 100 and/or the second tank 200.

In an embodiment of the disclosure, the solution mixing apparatus 10 may further include a controller 940 electrically connected to the sampling element 300, the flow control element 350, the first air-intake system 500, the first air-exhaust system 600, the second air-intake system 700, the second air-exhaust system 800, and the valves. The controller 940 serves to control the operations of the sampling element 300, the flow control element 350, the first air-intake system 500, the first air-exhaust system 600, the second air-intake system 700, the second air-exhaust system 800, and the valves. In order to clearly describe the connection relationship of the pipeline, the conduits, and other pipes, the electrical connection relationship between the controller and each controlled element is not limited, and the description herein is merely exemplary.

Figure 3:
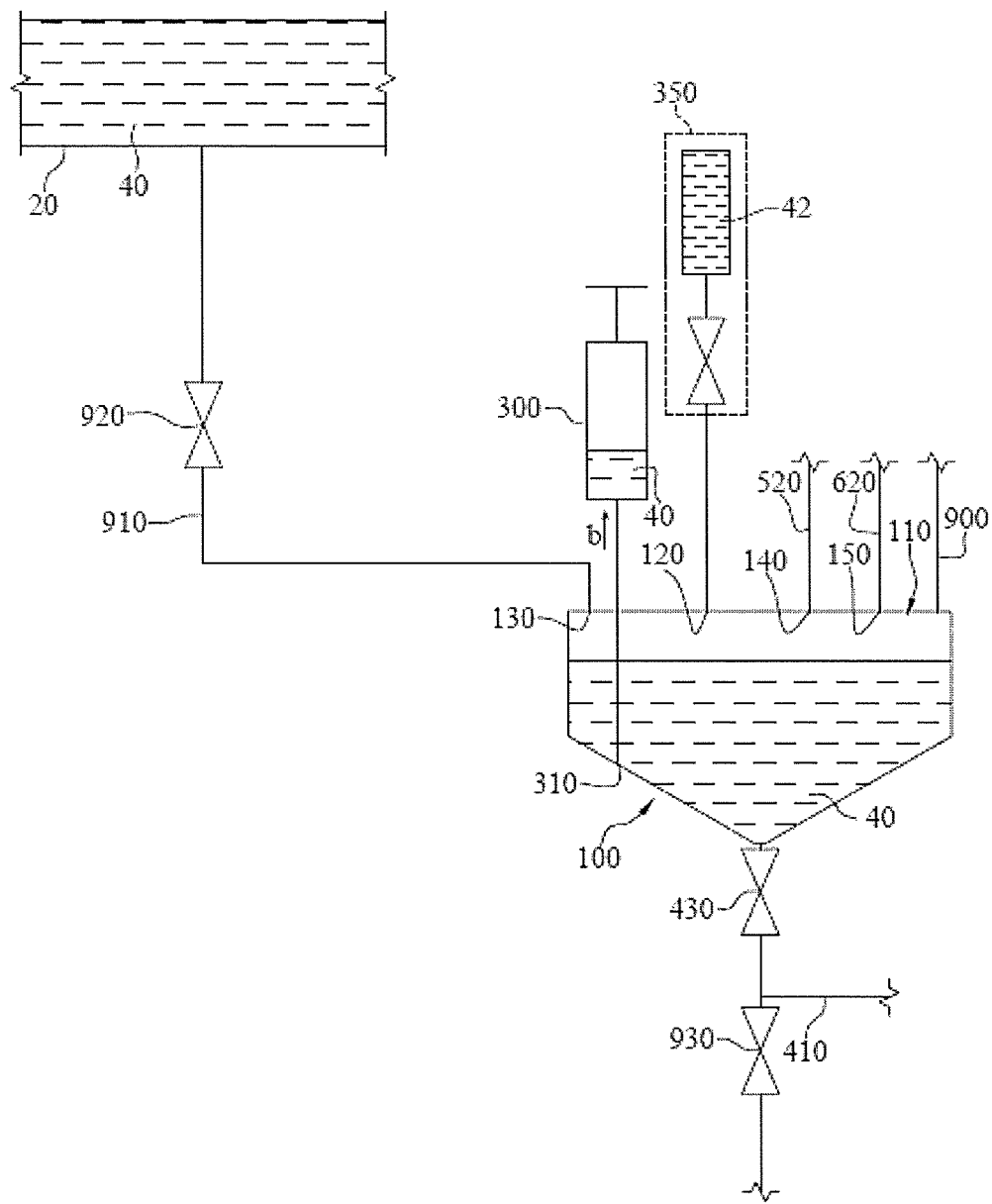
FIG. 3 is a schematic diagram illustrating that a sampling element extracts a first solution through an extraction port.
Figure 4:
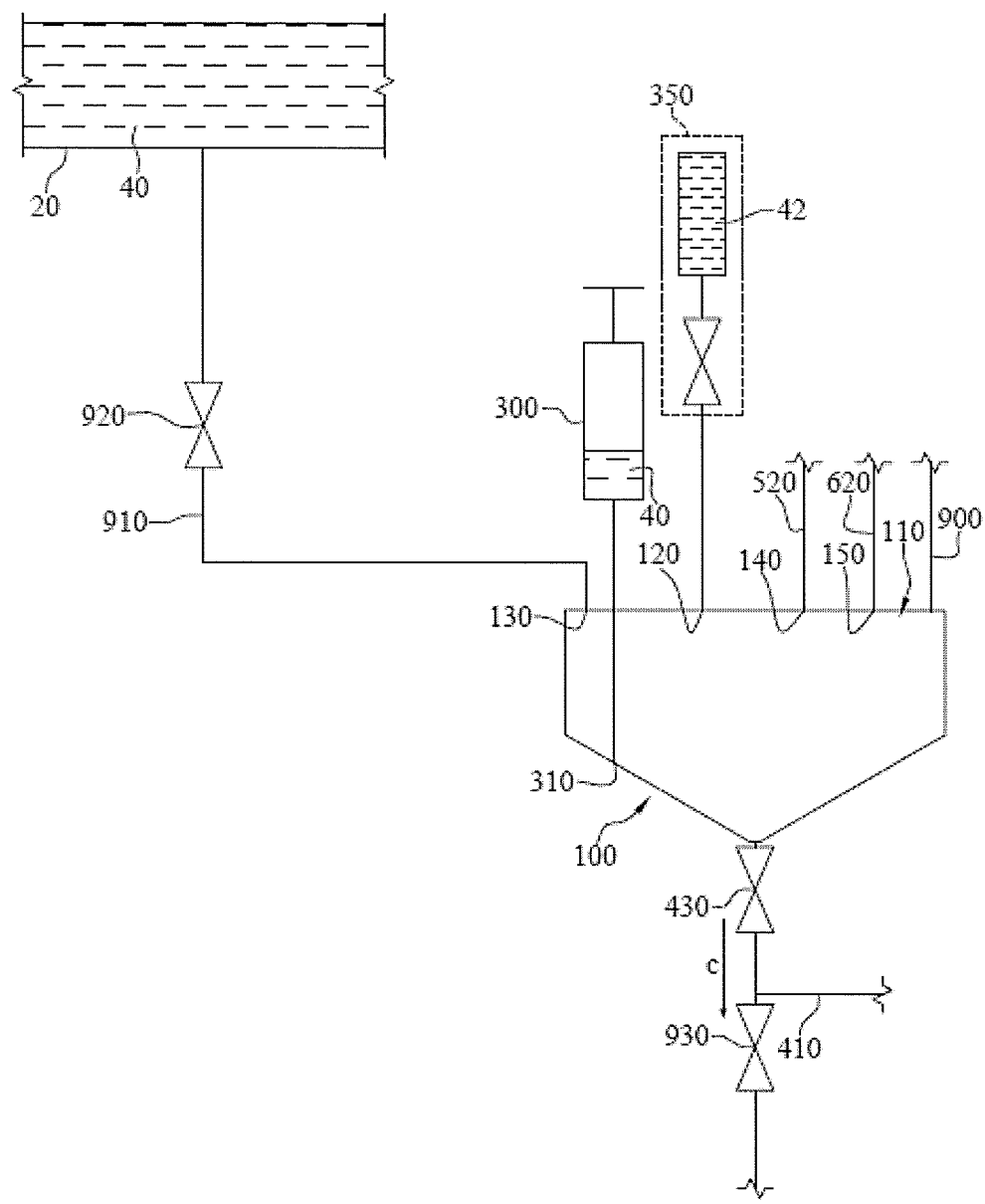
FIG. 4 is a schematic planar diagram illustrating that a drain switch valve drains a first solution from a first chamber.
Figure 5:
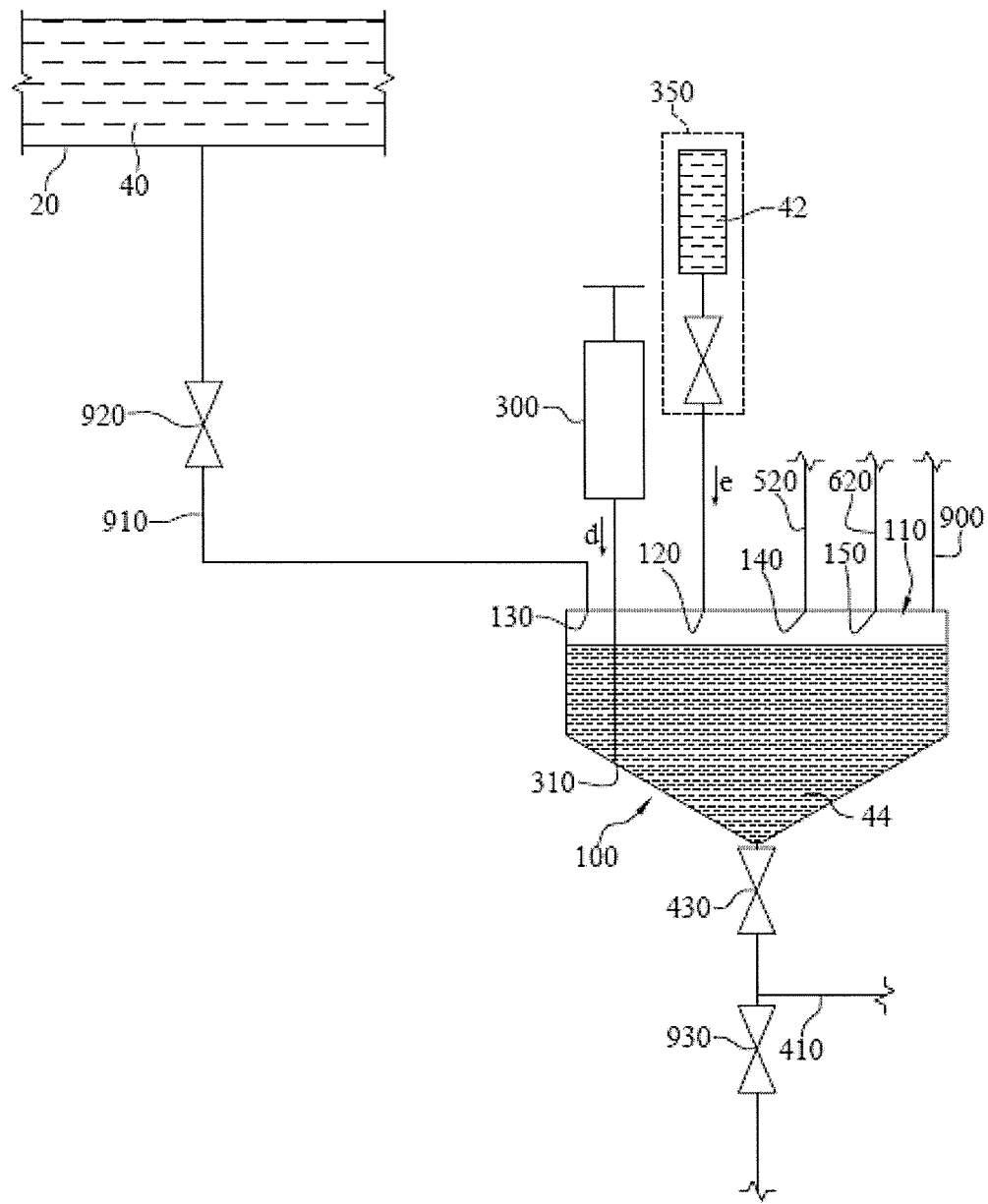
FIG. 5 is a schematic planar diagram illustrating that a second solution in a flow control element is infused into a first chamber through a first fluid inlet, as well as the extracted first solution is re-infused into a first chamber through an extraction port.
Figure 6:
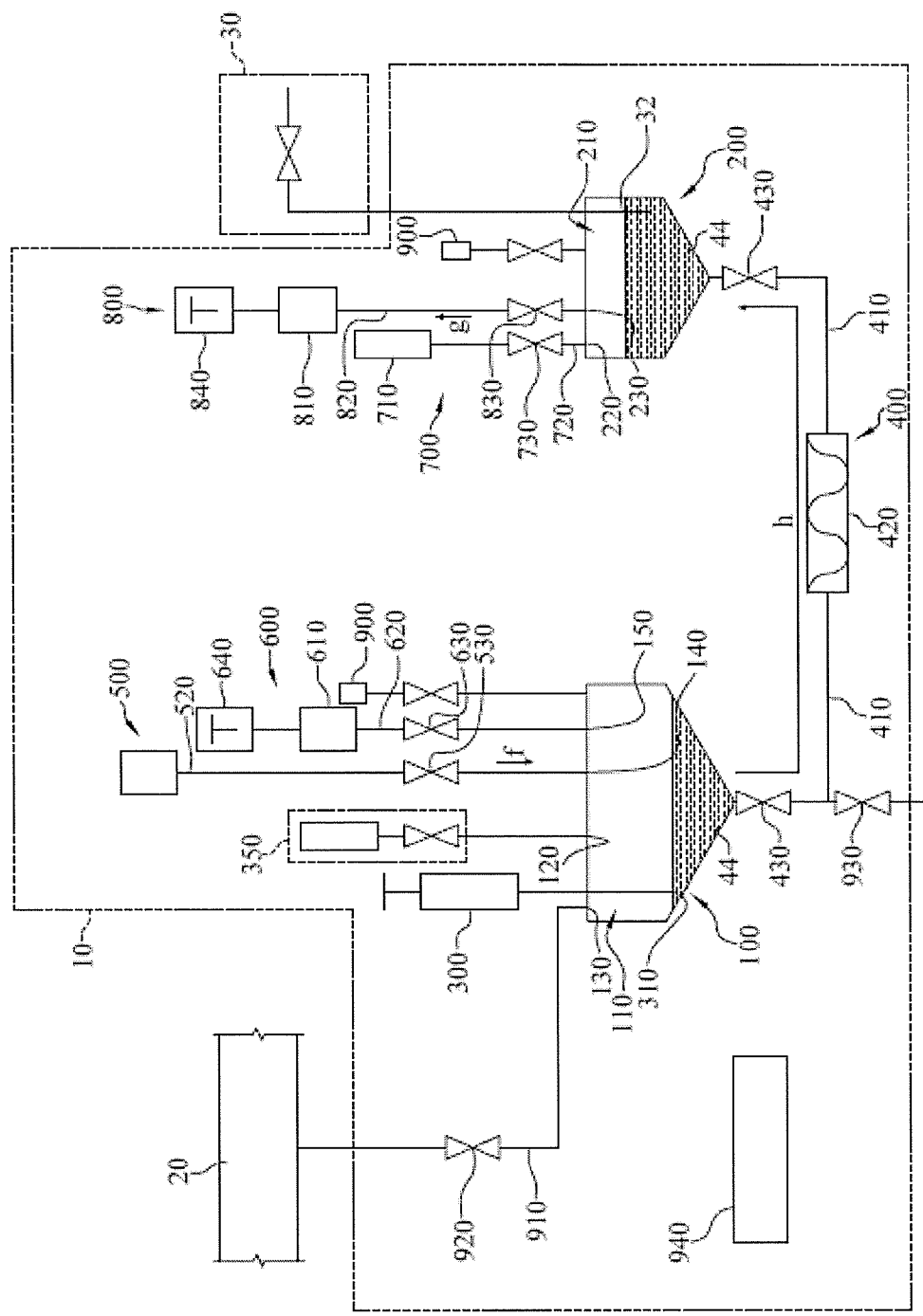
FIG. 6 is a schematic planar diagram illustrating that air-intake and air-exhaust systems drive a third solution to flow from a first chamber to a second chamber.
Figure 7:
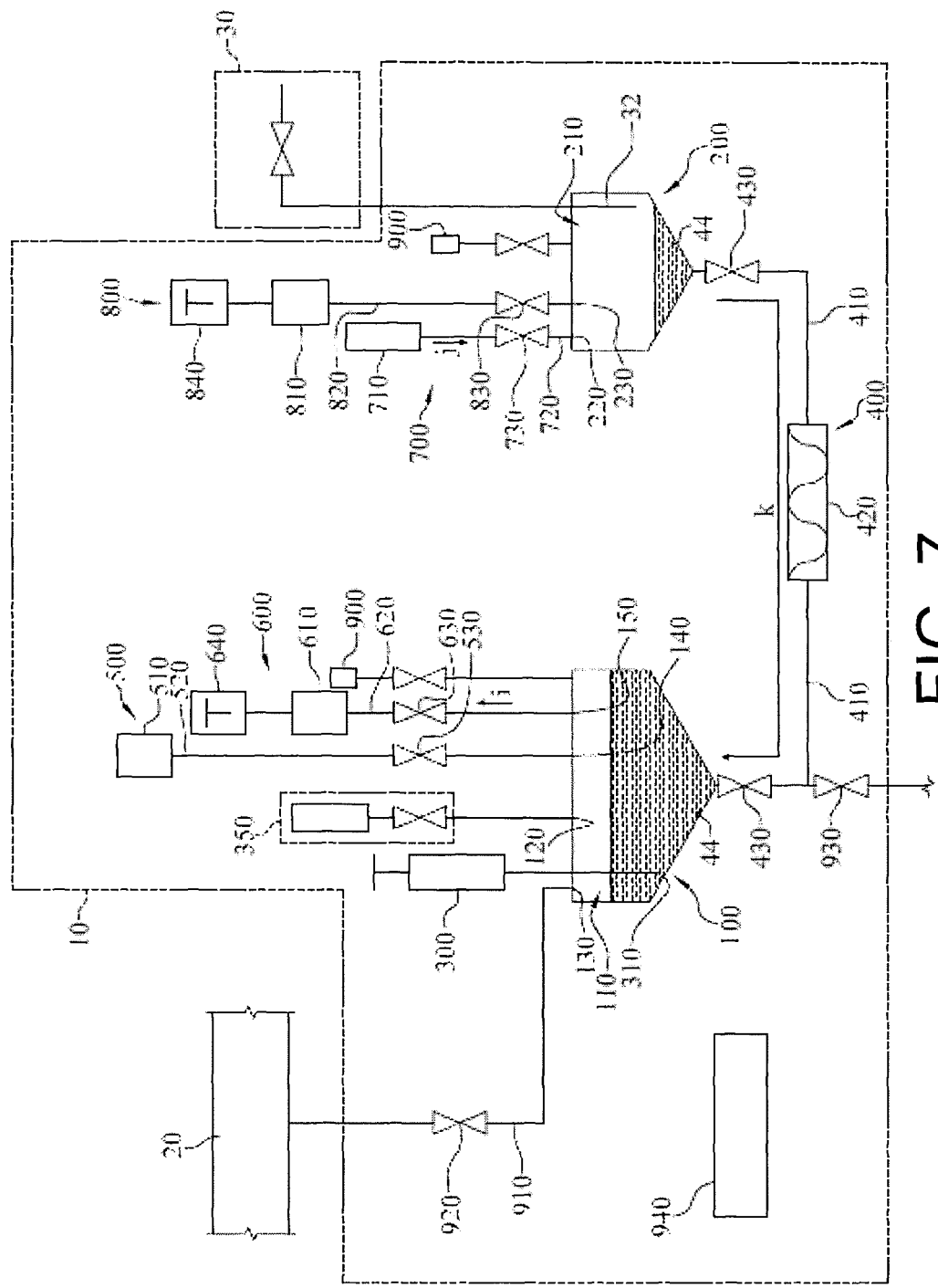
FIG. 7 is a schematic planar diagram illustrating that the air-intake and air-exhaust systems drive the third solution to flow back to the first chamber from the second chamber.
Figure 8:
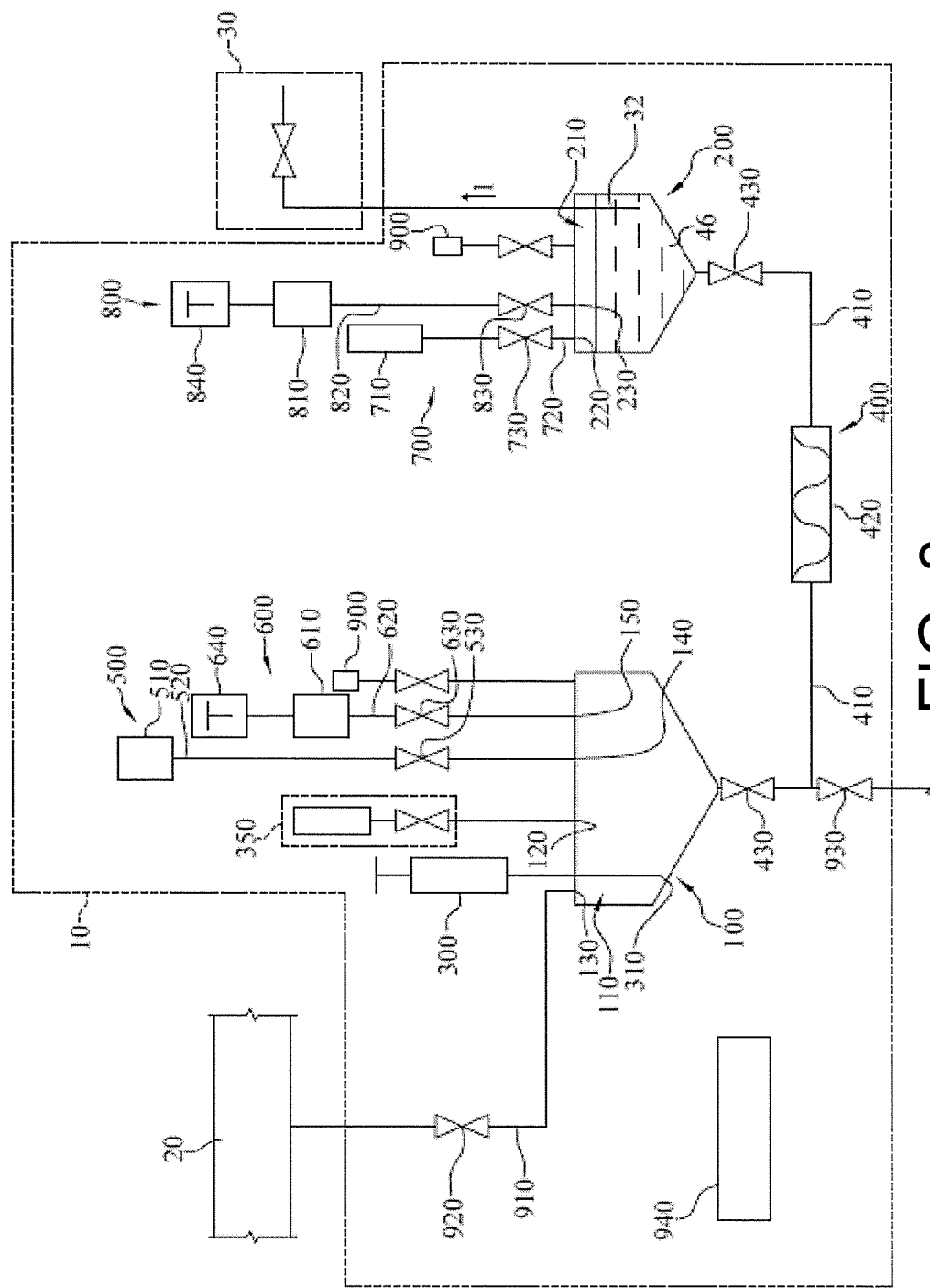
FIG. 8 is a schematic planar diagram illustrating that analysis equipment extracts a mixed fourth solution.

Please refer to FIG. 2 to FIG. 8. FIG. 2 is a schematic planar diagram illustrating that a first solution in a pipeline is infused into a first chamber through a second fluid inlet. FIG. 3 is a schematic diagram illustrating that a sampling element extracts a first solution through an extraction port. FIG. 4 is a schematic planar diagram illustrating that a drain switch valve drains a first solution from a first chamber. FIG. 5 is a schematic planar diagram illustrating that a second solution in a flow control element is infused into a first chamber through a first fluid inlet, as well as the extracted first solution is re-infused into a first chamber through an extraction port. FIG. 6 is a schematic planar diagram illustrating that air-intake and air-exhaust systems drive a third solution to flow from a first chamber to a second chamber. FIG. 7 is a schematic planar diagram illustrating that the air-intake and air-exhaust systems drive the third solution to flow back to the first chamber from the second chamber. FIG. 8 is a schematic planar diagram illustrating that analysis equipment extracts a mixed fourth solution.

In the present embodiment, the solution mixing apparatus 10 is controlled by the controller 940, so as to achieve purposes of automatic sampling, dilution, mixing, cleansing, and analysis, while the disclosure is not limited thereto; in another embodiment, the solution mixing apparatus 10 can also be manually controlled. Hence, the control mechanism of the controller 940 will not be further explained below.

As shown in FIG. 2, the second switch valve 430 is closed, and the first switch valve 920 is opened, such that the first solution 40 in the pipeline 20 is infused into the first chamber 110 (possibly in a direction shown by the arrow a).

As shown in FIG. 3, both the first switch valve 920 and the second switch valve 430 are closed. The sampling element 300 extracts the first solution 40 from the first chamber 110 through the extraction port 310 (possibly in a direction shown by the arrow b), so as to complete the sampling action. Here, the amount of extraction can be determined according to actual requirements, e.g., may be within a range from 0.1 ml to 10 ml. Through the sampling element 300, the amount of extraction of the first solution 40 can be controlled in a consistent manner. For instance, if the sampling element 300 is a syringe, the extraction amount of the syringe is proportional to a pulling or pushing distance of the piston of the syringe; if the pulling or pushing distance of the piston stays unchanged, the extraction amount of the syringe also remains unchanged, and thereby the consistency of each analysis result can be ensured. Although the accuracy of the extraction amount of the syringe may not be completely guaranteed, the deviation is within a tolerable range.

As shown in FIG. 4, both the second switch valve 430 and the drain switch valve 930 are opened, such that the remaining first solution 40 in the first chamber 110 is drained out through the drain switch valve 930 (possibly in a direction shown by the arrow c).

In an embodiment of the disclosure, after the remaining first solution 40 is drained out, the first chamber 110 can be further cleansed by the cleansing equipment 900, so as to further ensure the accuracy of the analysis result.

As shown in FIG. 5, both the second switch valve 430 and the drain switch valve 930 are closed. The sampling element 300 re-infused the extracted first solution 40 back into the first chamber 110 (possibly in a direction shown by the arrow d). The flow control element 350 infuses a second solution 42 into the first chamber 110 (possibly in a direction shown by the arrow e) and controls an infusion amount of the second solution 42, so as to obtain a third solution 44 (containing the first solution 40 and the second solution 42). In the present embodiment, the infusion amount of the first solution 40 is 1 ml, for instance, and the infusion amount of the second solution 42 is 500 ml, for instance, such that the ratio of the first solution 40 (e.g., slurry) to the second solution (e.g., a diluted solution) reaches 1:500. However, the disclosure is not limited thereto; in other embodiments of the disclosure, the ratio of the first solution 40 to the second solution may range from 1:10 to 1:5000.

The steps shown in FIG. 2 to FIG. 5 may evidence the implementation of constant-amount sampling and the action of diluting the sample to obtain a solution with the predetermined concentration. However, said sampling method is merely exemplary and should not be construed as a limitation to the disclosure. As to the constant-amount sampling, it is not limited in the present embodiment that the first solution 40 is infused into the first chamber 110, the sample with the fixed amount is extracted by the sampling element 300, the first chamber 110 is cleansed, and the first solution 40 in the sampling element 300 is re-infused into the first chamber 110.

Figure 10A:
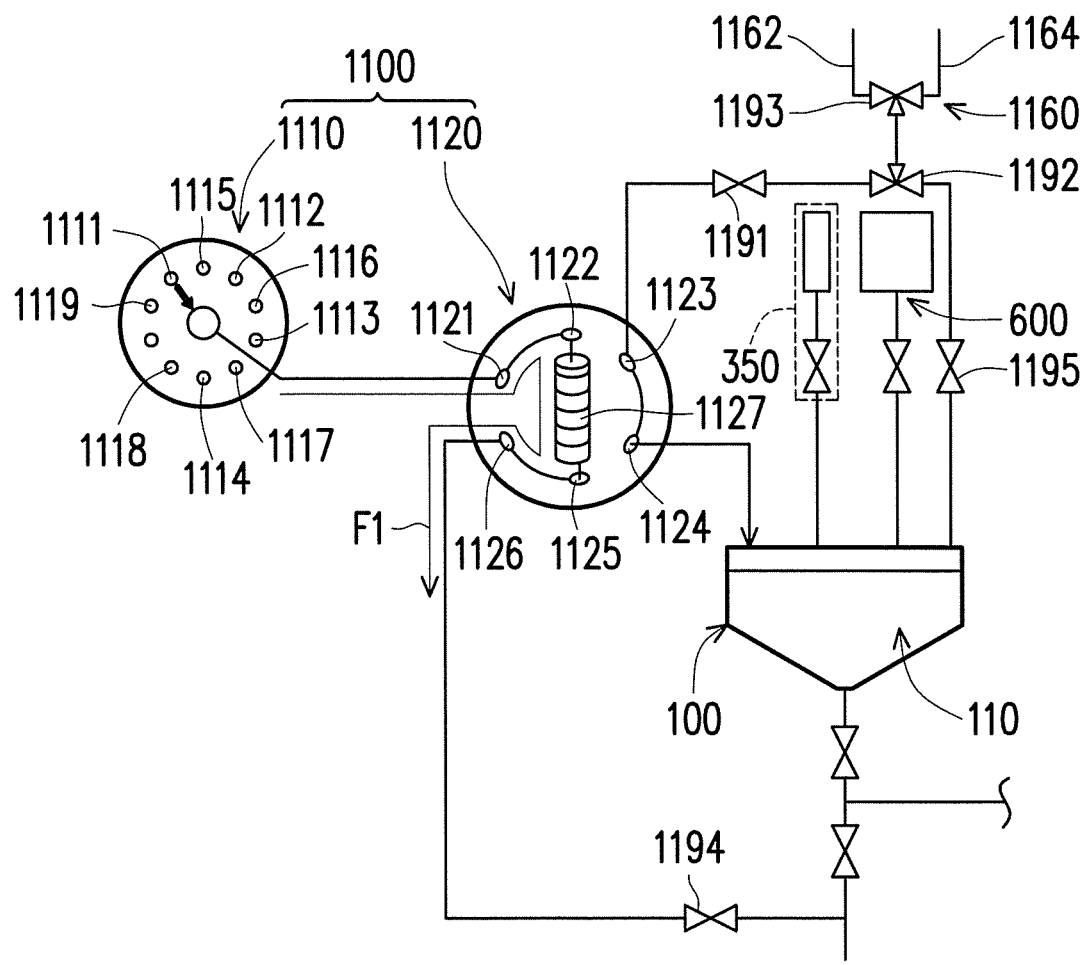
FIG. 10A and FIG. 10B further illustrate a specific structure and operation of another sampling element applicable in the embodiments of the disclosure.
Figure 10B:
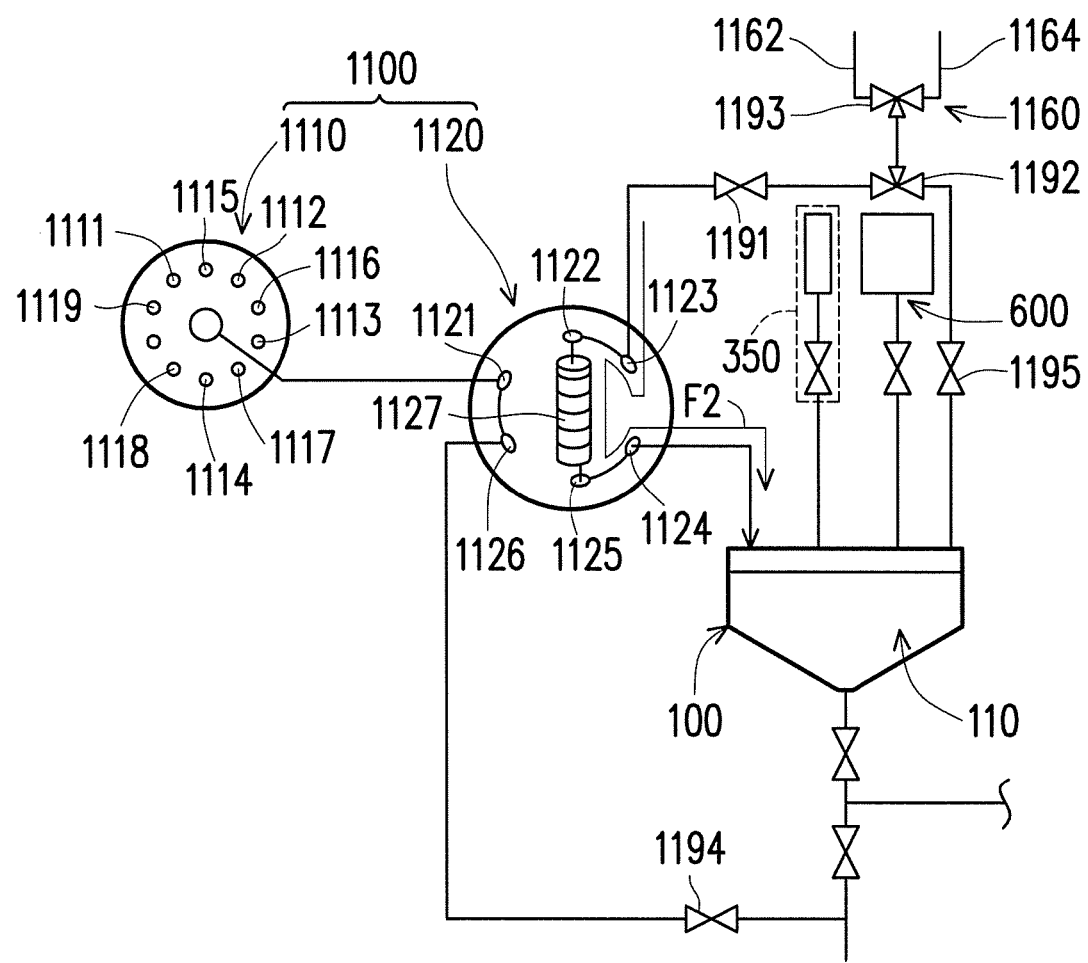

For instance, FIG. 10A and FIG. 10B further illustrate a specific structure and operation of another sampling element applicable in the embodiments of the disclosure. That is, the sampling element depicted in FIG. 10A and FIG. 10B may replace the aforesaid sampling element 300. According to the present embodiment, the sampling element 1100 may include an inlet valve 1110 and a sampling valve 1120. When the sampling element 1100 provided in the present embodiment is applied to the solution mixing apparatus 10 shown in FIG. 1, the sampling valve 1120 connects and communicates with the first chamber 110; besides, as shown in FIG. 10A and FIG. 10B, the flow control element 350, the first air-exhaust system 600, and the cleansing equipment 1160 are all connected to the first tank 100. The cleansing equipment 1160 provided herein is not only connected to the first tank 100 but also connected to the sampling valve 1120. Certainly, in the present embodiment, the cleansing equipment 900 shown in FIG. 1 and connected to the first tank 100 may also be arranged.

The inlet valve 1110 may be connected to the sampling valve 1120 and may have a plurality of sample infusion ports 1111 to 1114, a plurality of flush infusion ports 1115 to 1118, and a clean dry air (CDA) infusion port 1119, for instance. Based on actual requirements, different samples, flushes, or CDA may be infused into the sampling valve 1120 through the sample infusion ports 1111 to 1114. In an embodiment of the disclosure, the sample infusion ports 1111 to 1114 may be respectively connected to a plurality of pipes, so as to infuse and monitor a plurality of samples.

The sampling valve 1120 may be equipped with a plurality of valve ports 1121 to 1126 and a sample loop 1127. It is possible to switch the sampling valve 1120 to change the connection status among valve ports 1121 to 1126. The inlet valve 1110 is connected to the valve port 1121. The sample loop 1127 is connected between the valve ports 1122 and 1125. The valve port 1123 connects and communicates with the cleansing equipment 1160 through valves 1191 to 1193. The valve port 1124 connects and communicates with the first tank 100. The valve port 1126 connects and communicates with the drain end through a valve 1194.

Identical to the previous embodiments, the present embodiment discloses that the flow control element 350 may serve to infuse de-ionized water or other diluted solutions into the first tank 100, so as to dilute the sample in the first tank 100. Identical to the previous embodiments, the present embodiment discloses that the first air-exhaust system 600 may serve to exhaust air from the first tank 100, so as to lower the air pressure in the first tank 100.

The cleansing equipment 1160 may be respectively connected to the CDA and the flush through the conduits 1162 and 1164, for instance. The cleansing equipment 1160 connects and communicates with the valve port 1123 through the valve 1191 and connects and communicates the first tank 100 through the valve 1195. Through controlling the valves 1192 and 1193, the CDA or the flush may be alternatively infused to the sampling valve 1120 and/or the first tank 100. Particularly, in the present embodiment, the CDA may be infused into the first tank 100 through the conduit 1162, so as to increase the air pressure in the first chamber 110. The infused air may be compressed air, nitrogen, or an inert gas, for instance. Alternatively, the flush may be infused into the sampling valve 1120 and/or the first tank 100 through the conduit 1164, so as to clean out the residual sample (solution).

Besides, the way to switch the sampling valve 1120 is described below. The sampling valve 1120 is switched to the state shown in FIG. 10A. At this time, the valve port 1121 connects and communicates with the valve port 1122, the valve port 1123 connects and communicates with the valve port 1124, and the valve port 1125 connects and communicates with the valve port 1126. In addition, the valve port 1122 does not connect and communicate with the valve port 1123, the valve port 1124 does not connect and communicate with the valve port 1125, and the valve port 1126 does not connect and communicate with the valve port 1121. At this time, the inlet valve 1110 may provide the sample to the sampling valve 1120 though one of the sample infusion ports 1111 to 1114 (e.g., the sample infusion port 1111). The sample can be infused into the sample loop 1127 through the valve ports 1121 and 1122. In the state shown in FIG. 10A, the valve port 1121, the valve port 1122, the sample loop 1127, the valve port 1125, and the valve port 1126 connect and communicate with one another, such that the sample flows along the flow path F1 after entering into the sample valve 1120. To ensure the sample loop 1127 to be filled with the sample, the sample may be continuously infused, and the surplus sample may continue flowing along the flow path F1 and may then be drained out through the drain end. That is, the step shown in FIG. 10A helps ensure the sample loop 1127 to be filled with the sample.

The sampling valve 1120 can then be switched to the state shown in FIG. 10B. At this time, the valve port 1122 connects and communicates with the valve port 1123, the valve port 1124 connects and communicates with the valve port 1125, and the valve port 1126 connects and communicates with the valve port 1121. In addition, the valve port 1121 does not connect and communicate with the valve port 1122, the valve port 1123 does not connect and communicate with the valve port 1124, and the valve port 1125 does not connect and communicate with the valve port 1126. Thereby, the flow path F2 may be defined to perform the step of infusing the sample into the first tank 100.

Specifically, when the step of infusing the sample is performed, the CDA from the conduit 1162 may be infused into the sample loop 1127 along the flow path F2, so as to push the sample in the sample loop 1127 along the flow path F2. Thereby, the sample in the sample loop 1127 is sequentially infused into the first tank 100 through the valve ports 1125 and 1124. In this step, the infusion amount of CDA from the conduit 1162 can be controlled, so as to adjust the volume of the sample infused into the first tank 100. Through the steps shown in FIG. 10A and FIG. 10B, the volume of the sample infused into the first tank 100 can be accurately controlled. Based on said descriptions, people having ordinary skill in the art should be able to, by applying the existing technology, perform the automatic sampling function and the pre-treatment function (for example, diluting and/or mixing) through combining the sampling element 1100 provided herein with the second tank 200, the mixing assembly 400, the second air-intake system 700, the second air-exhaust system 800, the cleansing equipment 900, and the controller 940. Relevant explanations are provided in the previous embodiments and thus will not be further given hereinafter.

After the step of infusing the sample with the fixed amount (e.g., the first solution 40) and the second solution 42 is preformed, as shown in FIG. 6 and FIG. 7, a pressure difference between the first chamber 110 and the second chamber 210 is generated through the first air-intake system 500, the first air-exhaust system 600, the second air-intake system 700, and the second air-exhaust system 800, such that the first solution 40 and the second solution 42 are enabled to repeatedly flow through the mixing assembly 400 between the first chamber 110 and the second chamber 210, and that the mixing effects can be achieved.

As shown in FIG. 6, the first air-intake valve 530, the second air-exhaust valve 830, and two second switch valves 430 are opened, and the drain switch valve 930 is closed. The first air-intake system 500 infuses air into the first chamber 110 through the first air-intake port 140 (possibly in a direction shown by the arrow f), and the second air-exhaust system 800 exhausts air from the second chamber 210 through the second air-exhaust port 230 (possibly in a direction shown by the arrow g), such that the pressure in the first chamber 110 is greater than that in the second chamber 210, and that the third solution 44 is driven to flow from the first chamber 110 to the second chamber 210 (possibly in a direction shown by the arrow h); however, the disclosure is not limited thereto. In other embodiments of the disclosure, it is possible to merely enable the first air-intake system 500 to infuse air into the first chamber 110 or merely enable the second air-exhaust system 800 to exhaust air from the second chamber 210 (as long as the pressure in the first chamber 110 is greater than that in the second chamber 210).

As shown in FIG. 7, the second air-intake system 700 infuses air into the second chamber 210 through the second air-intake port 220 (possibly in a direction shown by the arrow j), and the first air-exhaust system 600 exhausts air from the first chamber 110 through the first air-exhaust port 150 (possibly in a direction shown by the arrow i), such that the pressure in the second chamber 210 is greater than that in the first chamber 110, and that the third solution 44 is driven to flow from the second chamber 210 to the first chamber 110 (possibly in a direction shown by the arrow k); however, the disclosure is not limited thereto. In other embodiments of the disclosure, it is possible to merely enable the second air-intake system 700 to infuse air into the second chamber 210 or merely enable the first air-exhaust system 600 to exhaust air from the first chamber 110 (as long as the pressure in the second chamber 210 is greater than that in the first chamber 110).

Here, the air is infused into the first chamber 110 and the second chamber 210 that can accommodate fluids, and thereby the fluids in the first chamber 110 or in the second chamber 210 may flow through the mixer 420; as a result, the mixing effects achieved by the solution mixing apparatus 10 can be further enhanced.

Steps shown in FIG. 6 and FIG. 7 may be repeated at least once, so as to obtain a well-mixed fourth solution 46 (as shown in FIG. 8). The analysis equipment 30 extracts the well-mixed fourth solution 46 through the sampling end 32 (possibly in a direction shown by arrow l) for analysis.

The effects of mixing the third solution 44 is relevant to the length of the mixer 420; the greater the length of the mixer 420, the better the effects of mixing the third solution 44. However, in order to miniaturize the solution mixing apparatus 10, the size of the mixer 420 in the solution mixing apparatus 10 described herein cannot be expand without limitation. Given the limited size of the mixer 420, the solution mixing apparatus 10 provided in the present embodiment allows the air-intake and air-exhaust systems to drive the third solution 44 to repetitively flow through the mixer 420, such that the number of times of the third solution 44 flowing through the mixer 420 can be increased. That is, the increase in the number of times of the third solution 44 flowing through the mixer 420 may compensate for the reduction of the mixing effects caused by the insufficient size of the mixer 420, and the requirements for miniaturizing the solution mixing apparatus 10 and enhancing the mixing effects of the solution mixing apparatus 10 can both be satisfied.

Figure 9:
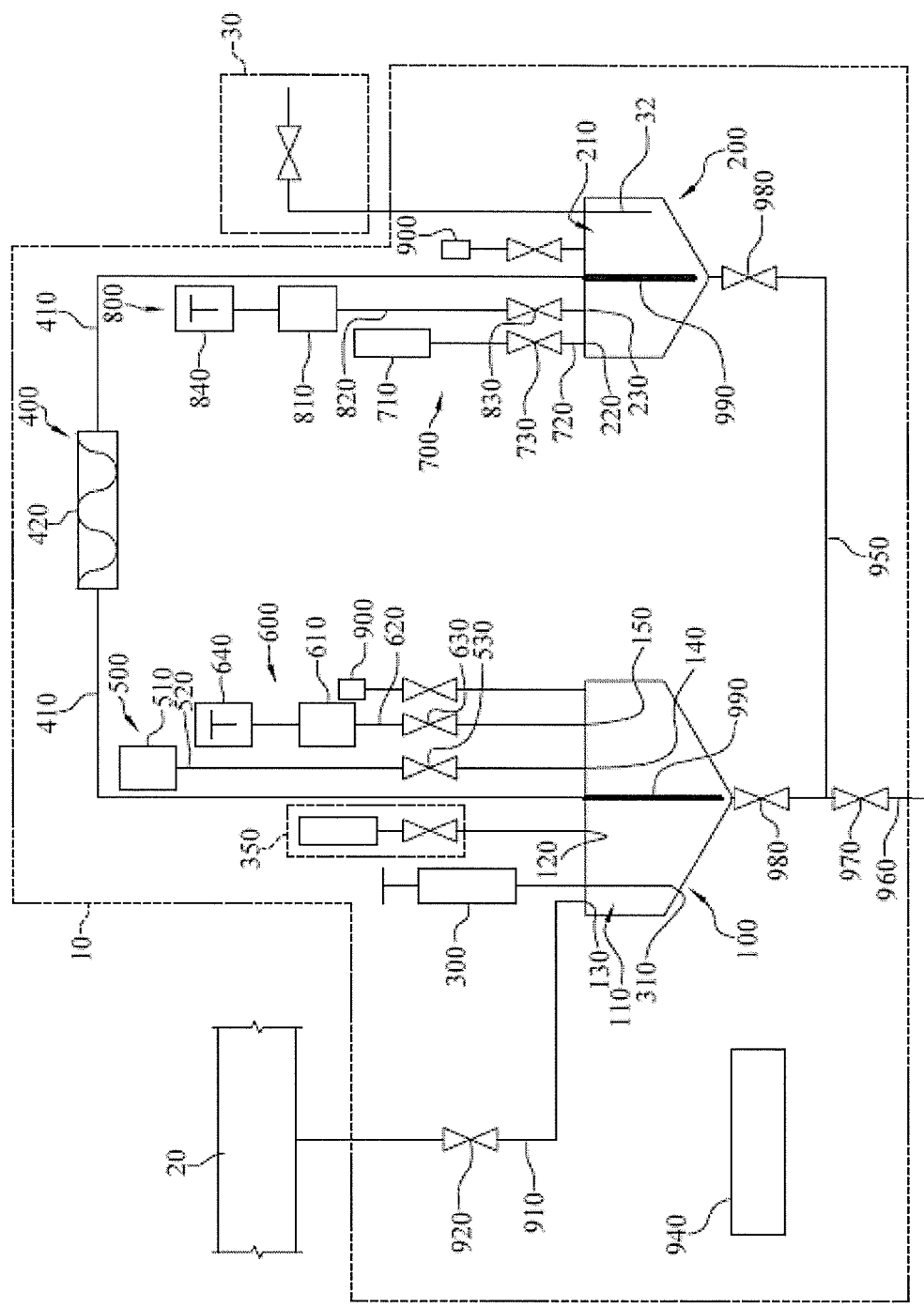
FIG. 9 is a schematic systematic diagram illustrating a solution mixing apparatus connected to a pipeline and analysis equipment according to another embodiment of the disclosure.

Please refer to FIG. 9. FIG. 9 is a schematic systematic diagram illustrating a solution mixing apparatus connected to a pipeline and analysis equipment according to another embodiment of the disclosure. The present embodiment is similar to the previous embodiment, and therefore only the differences are explained hereinafter.

In the previous embodiment, the pipes for the mixing purpose and for the draining purpose are the same, while the pipes for said two purposes are separated in the present embodiment. Separation of the pipes further guarantees the consistency of the mixing quality of the solution mixing apparatus 10.

In the present embodiment, the solution mixing apparatus 10 may further include a connection conduit 950, a drain conduit 960, and a drain switch valve 970, and two opposite ends of the connection conduit 950 respectively connect and communicate with the first chamber 110 and the second chamber 210. The drain conduit 960 connects and communicates with the connection conduit 950. The drain switch valve 970 is arranged on the drain conduit 960 for enabling or disabling flow into or out of the drain conduit 960.

In the present embodiment, the solution mixing apparatus 10 may further include two third switch valves 980 arranged on the two opposite ends of the connection conduit 950 for enabling or disabling flow into or out of the connection conduit 950.

The two second conduits 410 of the mixing assembly 400 respectively connect and communicate with the first chamber 110 and the second chamber 210 through two fluid extraction pipes 990.

If fluids are to be mixed, the fluids flow from the fluid extraction pipes 990 and the second conduits 410 to the mixer 420. However, when the fluids are to be drained out, the fluids flow through the connection conduit 950, the drain conduit 960, and the drain switch valve 970, which evidences that the conduits or pipes for the mixing purpose and for the draining purpose are separated.

According to an embodiment of the disclosure, the solution mixing apparatus and the method of mixing a solution allow the air-intake and air-exhaust systems to drive the solution to repetitively flow through the mixer, such that the number of times of the solution flowing through the mixer can be increased. Thereby, the increase in the number of times of the solution flowing through the mixer may compensate for the reduction of the mixing effects caused by the insufficient size of the mixer, and the requirements for miniaturizing the solution mixing apparatus and enhancing the mixing effects of the solution mixing apparatus can both be satisfied.

The mixer is a static mixer, for instance, and the mixer is capable of preventing particles from aggregating or falling off, so as to keep the original particle size distribution of sample solution after diluting and mixing.

In addition, the air conduit and the fluid conduit are the same; if the air flows, the fluids in the fluid conduit are driven to flow as well. Thereby, all fluids in the fluid conduit can be fully mixed, and the mixing effects of the solution mixing apparatus can be further ameliorated.

The solution diluted and mixed by applying the solution mixing apparatus and the method of mixing the solution, as described in the previous embodiments, is provided to analysis equipment for analysis. If the analysis equipment is integrated into the solution mixing apparatus, in an embodiment of the disclosure, an apparatus for monitoring particles in a solution can be provided, so as to meet the requirements for automation and for on-line monitoring of various particles (e.g., nano-particles) in the solution.

FIG. 11 is a schematic diagram illustrating an apparatus for monitoring particles in a solution according to an embodiment of the disclosure. As shown in FIG. 11, an apparatus 1000 for monitoring particles in a solution may include a solution mixing apparatus 1210 and analysis equipment 1220. The solution mixing apparatus 1210 provided herein may be the solution mixing apparatus 10 shown in FIG. 1 to FIG. 9 or may be implemented by employing parts or components in the solution mixing apparatus 10, and the sampling element 300 in the solution mixing apparatus 10 can be alternatively replaced by the sampling element 1100 shown in FIG. 10A and FIG. 10B according to actual requirements. That is, the solution mixing apparatus 1210 is able to perform the sampling step, the dilution step, the mixing step, and so on. In addition, the analysis equipment 1220 includes an aerosolization apparatus 1300, a particle size classifier 1400, and a particle counter 1500. The analysis equipment 30 described the previous embodiments may be replaced by the analysis equipment 1220 constituted by the aerosolization apparatus 1300, the particle size classifier 1400, and the particle counter 1500; however, the disclosure is not limited thereto.

When the solution mixing apparatus 1210 is equipped with the sampling element 1100 shown in FIG. 10A and FIG. 10B, for instance, a method of operating the apparatus 1000 for monitoring particles in the solution includes steps of infusing a tested solution having nano particles into the sampling element 1100 and extracting the first solution 40 with the predetermined volume by the sampling element 1100. Here, the diameter of each nano particle in the to-be-tested solution is from about 1 nm to about 1000 nm, for instance. The first solution 40 is diluted and mixed at a predetermined ratio by the solution mixing apparatus 1210, so as to obtain the resultant sample solution which has undergone pre-treatment. The sample solution is then extracted by the solution mixing apparatus 1210 and provided to the aerosolization apparatus 1300, for instance.

Figure 12:
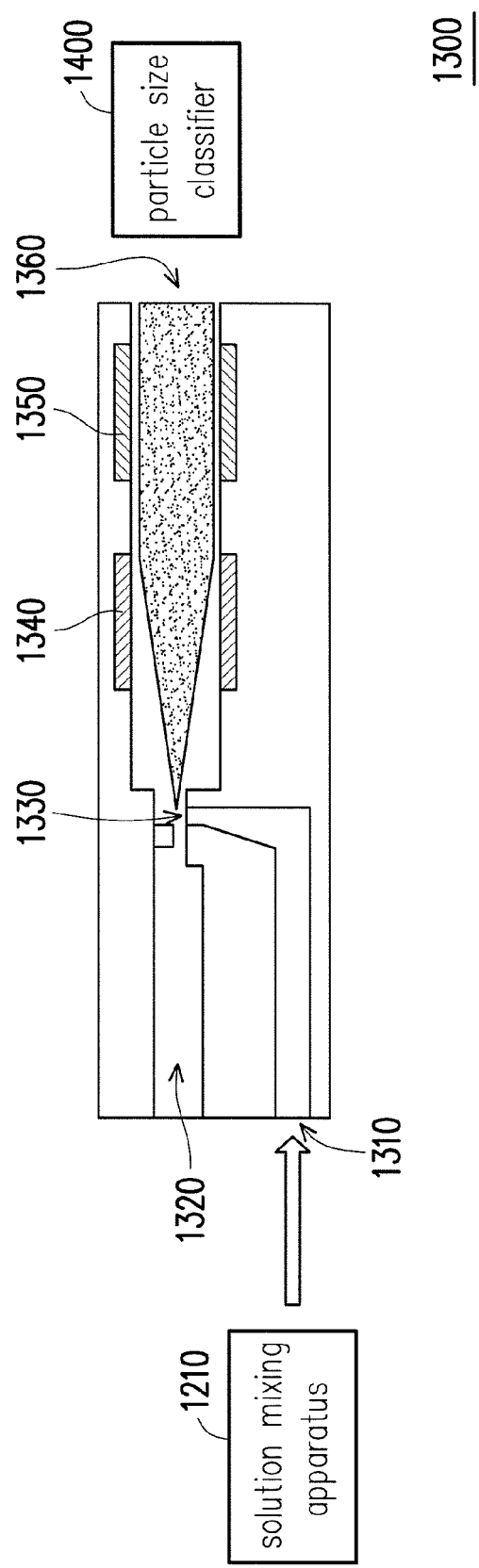
FIG. 12 is a schematic diagram illustrating an aerosolization apparatus according to an embodiment of the disclosure.

FIG. 12 is a schematic diagram illustrating an aerosolization apparatus according to an embodiment of the disclosure. In a present embodiment, the aerosolization apparatus may be an electrospray, an ultrasonic nebulizer, an atomizer, or any droplet generator.

The aerosolization apparatus 1300 described herein is the atomizer, for instance. With reference to FIG. 12, the aerosolization apparatus 1300 includes a sample solution guiding inlet 1310, a high-pressure air guiding inlet 1320 and an aerosolized aperture 1330 constituting an aerosolization generator, a heating element 1340, a drying element 1350, and an aerosolized particle guiding outlet 1360. The sample solution guiding inlet 1310 connects and communicates with the solution mixing apparatus 1210, and the sample solution which has undergone the pre-treatment enters the aerosolization apparatus 1300 through the sample solution guiding inlet 1310. The aerosolized particle guiding outlet 1360 may be opposite to the sample solution guiding inlet 1310. The aerosolized aperture 1330 is located between the sample solution guiding inlet 1310 and the aerosolized particle guiding outlet 1360. The high-pressure air guiding inlet 1320 is connected to the aerosolized aperture 1330. The air pressure source required for aerosolization is provided to the aerosolized aperture 1330 through the high-pressure air guiding inlet 1320. The significant shearing rate resulting from the high-pressure air allows the sample solution to be atomized and converted into aerosolized particles. The heating element 1340 and the drying element 1350 are located behind the aerosolized aperture 1330, and the resultant aerosolized particles pass through the heating element 1340 and the drying element 1350, so as to remove the surplus solution on surfaces of the aerosolized particles. The aerosolized particles are then transmitted to the particle size classifier 1400 through the aerosolized particle guiding outlet 1360.

In the present embodiment, the heating element 1340 and the drying element 1350 may be arranged between the aerosolized aperture 1330 and the aerosolized particle guiding outlet 1360. However, in another embodiment of the disclosure, the heating element 1340 and the drying element 1350 may be located behind the aerosolized particle guiding outlet 1360, so as to achieve the same effects. In addition, the locations of the heating element 1340 and the drying element 1350 are not limited in the present embodiment. For instance, the location of the heating element 1340 shown in FIG. 12 may be exchanged with the location of the drying element 1350.

The atomizer provided in the present embodiment extracts the to-be-atomized sample solution by local pressure difference according to the Bernoulli's principle and bombards the sample solution through the aerosolized aperture 1330 by high-pressure air, such that the sample solution subject to the significant shearing force is separated into aerosolized particles. The resultant aerosolized particles, however, may be encapsulated by liquid films, such that the measured results are inconsistent with the actual conditions; in addition, droplets that do not contain the particles may be detected by end systems before the evaporation process is completed. Aforesaid phenomenon may easily cause measurement errors. Hence, in the present embodiment, the heating element 1340 and the drying element 1350 are arranged in front of or in the rear of the aerosolized particle guiding outlet 1360, so as to eliminate the influence of the droplets and the liquid films on the surfaces of the aerosolized particles.

Figure 13:
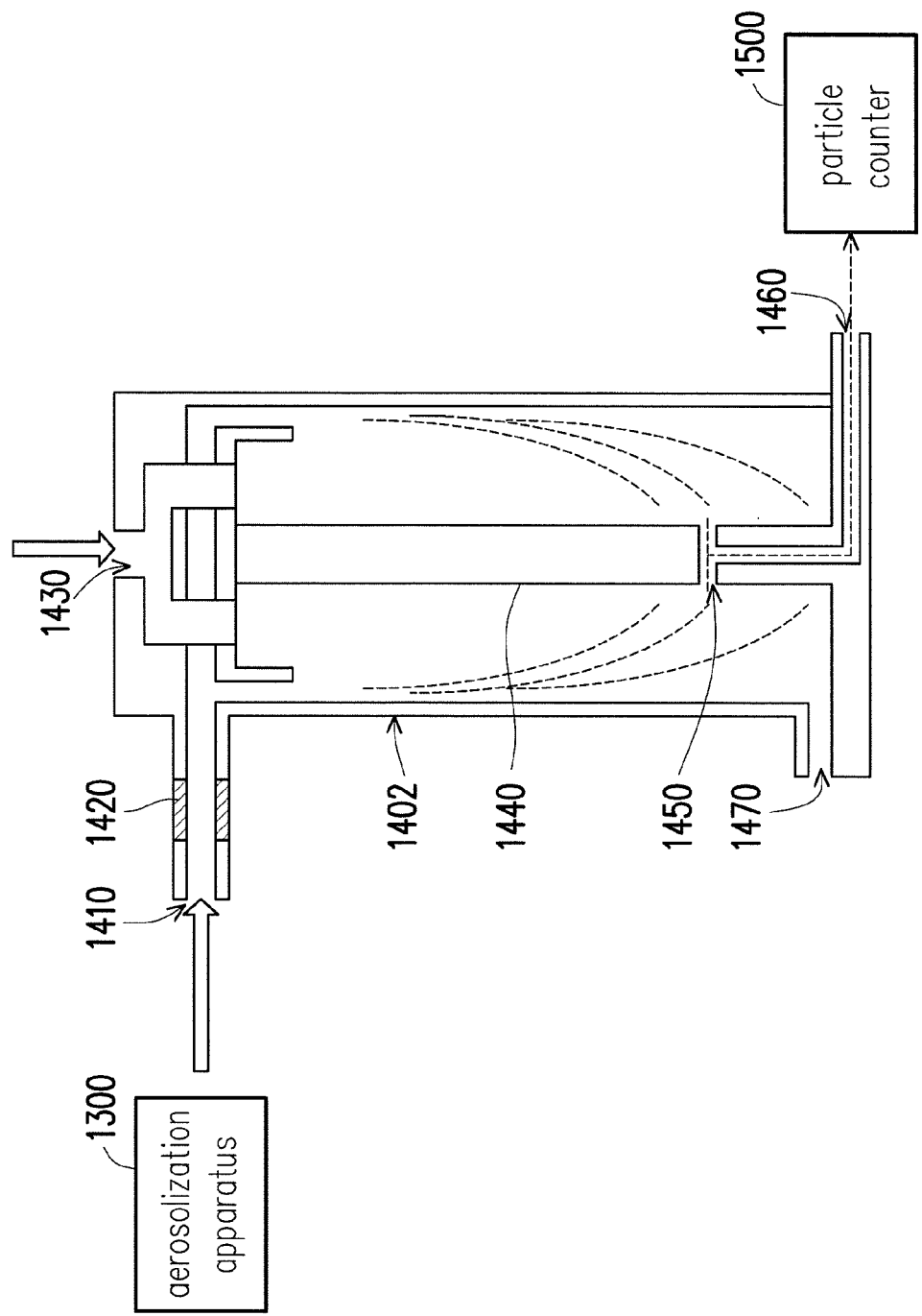
FIG. 13 is a schematic diagram illustrating a particle size classifier according to an embodiment of the disclosure.

FIG. 13 is a schematic diagram illustrating a particle size classifier according to an embodiment of the disclosure. In an embodiment of the disclosure, the particle size classifier may be a differential mobility analyzer, an electrostatic classifier, or a mass spectrometer. The particle size classifier 1400 provided in the present embodiment is, for instance, the differential mobility analyzer, and the particle size classifier 1400 classifies the charged particles mainly based on the difference in the electrical mobility of the aerosolized particles. Here, the particle size classifier 1400 includes an aerosolized particle guiding inlet 1410, a neutralizer 1420, a particle size classification chamber 1402, and an outlet 1460 of classified particles. The aerosolized particle guiding inlet 1410 connects and communicates with the aerosolized particle guiding outlet 1360 of the aerosolization apparatus 1300. The particle size classification chamber 1402 connects and communicates with the aerosolized particle guiding inlet 1410. The neutralizer 1420 is arranged between the aerosolized particle guiding inlet 1410 and the particle size classification chamber 1402. The aerosolized particles formed by aerosolizing the sample solution are sent to the aerosolized particle guiding inlet 1410; after passing through the neutralizer 1420, the aerosolized particles carry electrical charges that are evenly distributed. The particles then collide or rub against one another many times, and the charge distribution of the aerosolized particles is similar to the Boltzmann's distribution. Thereafter, the aerosolized particles enter the particle size classification chamber 1402. The particle size classification chamber 1402 has a sheath fluid guiding inlet 1430, and an electrode 1440 is located in the particle size classification chamber 1402. Here, the electrode 1440 may be shaped as a cylinder, for instance. Sheath air that is introduced into the particle size classification chamber 1402 through the sheath fluid guiding inlet 1430 brings the aerosolized particles to the bottom of the particle size classification chamber 1402; at this time, through the adjustment of the voltage of the electrode 1440, an electric field between the wall (e.g., the ground terminal) of the particle size classification chamber 1402 and the electrode 1440 (e.g., having the negative voltage) is generated, and the positively-charged aerosolized particles are attracted. The dragging force generated by the sheath air which drives the aerosolized particles and the attraction force of the electric field to the aerosolized particles are balanced, such that the aerosolized particles with certain electrical mobility are moved to a classification channel 1450 and are then collected. Hence, by changing plural sets of scan voltages, the aerosolized particles with different diameters can be classified. The outlet 1460 of the classified particles connects and communicates with the classification channel 1450, and the selected aerosolized particles are sent to the particle counter 1500 through the outlet 1460 for further calculation and analysis. In an embodiment of the disclosure, the particle size classifier 1400 may further include a surplus fluid outlet 1470 that connects and communicates with the particle size classification chamber 1402, and the surplus sheath air and particles are exhausted from the particle size classification chamber 1402 through the surplus fluid outlet 1470.

The differential mobility analyzer classifies the size of the particles based on the relevance between the electrical mobility and the diameters of the particles; nevertheless, the particles having different diameters and carrying different amount of electrical charges may have the same electrical mobility. Hence, before the classification process is performed based on the electrical mobility, the neutralizer 1420 may be applied to balance, control, and manage the charged particles, such that the charged particles can be distributed at a fixed distribution ratio. In the neutralizer 1420, the aerosolized particles carrying different amount of electrical charges may collide with highly concentrated bipolar ions due to the random thermal fluctuation, and thus the charged particles are distributed at a fixed distribution ratio, i.e., the ratio of the charged particles to the total particles is known. That is why the size distribution of the particles in the solution can be deduced from the number of particles measured by the particle counter 1500 in the subsequent analysis step.

Figure 14:
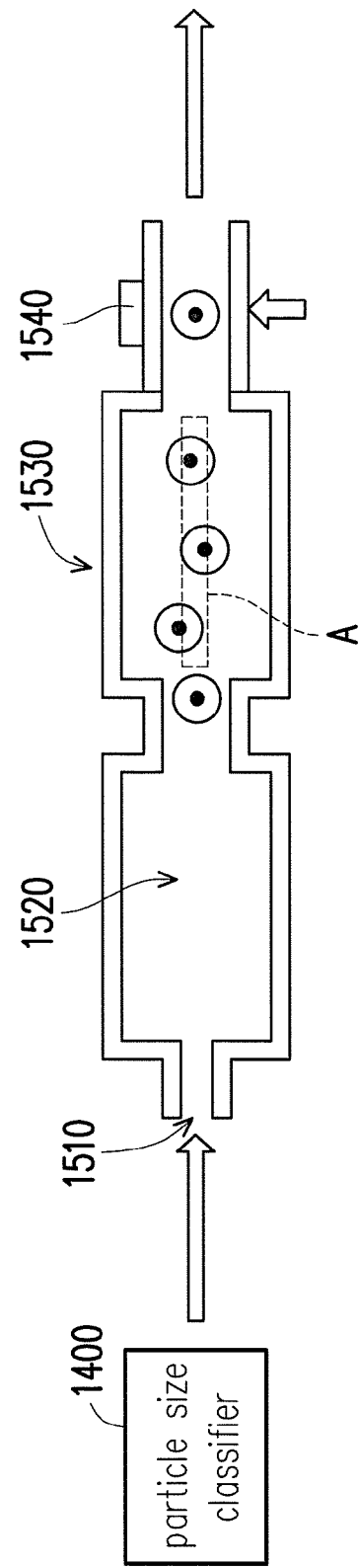
FIG. 14 is a schematic diagram illustrating a particle counter according to an embodiment of the disclosure.

FIG. 14 is a schematic diagram illustrating a particle counter according to an embodiment of the disclosure. The particle counter provided in an embodiment of the disclosure may be a condensation particle counter, a liquid particle counter, a discrete airborne particle counter, an electrometer, or the like. The particle counter 1500 described herein is the condensation particle counter, for instance. The condensation particle counter condenses the aerosolized particles which previously pass through a saturated vapor chamber, such that the aerosolized particles can absorb the vapor, and that a shell layer can be formed. The aerosolized particles can then be detected and analyzed by an optical counter. With reference to FIG. 14, the aerosolized particle guiding inlet 1510 connects and communicates with the outlet 1460 of classified particles of the particle size classifier 1400. The saturated vapor chamber 1520 may connect and communicate with the aerosolized particle guiding inlet 1510. The aerosolized particles that have been classified by the particle size classifier 1400 are sent to the aerosolized particle guiding inlet 1510. The saturated vapor chamber 1520 is filled with saturated vapor that is employed for forming the shell layer. A condenser 1530 connects and communicates with the saturated vapor chamber 1520. After the aerosolized particles pass through the saturated vapor chamber 1520, the surfaces of the aerosolized particles may absorb the vapor. After passing through the condenser 1530, the aerosolized particles are condensed to form particles having relatively large size and including the shell layer; therefore, these particles can be detected by a light source and light detection module 1540, so as to calculate the number of particles passing through the light source and light detection module 1540 and further analyze the particles.

In the present embodiment, the condensation particle counter (i.e., the particle counter 1500) is applied, such that the particles are, for instance, grown to 10 µm in form of condensed nuclei and then detected in an optical manner. The classified aerosolized particles may be served as the nucleation sites, passing through the supersaturated vapor, and then undergoing the condensation process, the particles may be further grown to large droplets. Said process is the so-called heterogeneous nucleation. In the condensation particle counter (i.e., the particle counter 1500), the supersaturation level of vapor can be accurately controlled to be at most at a threshold level, so as to prevent homogeneous nucleation of vapor, i.e., prevent generation of fluid inclusions carrying no particles.

The condensation particle counter (i.e., the particle counter 1500) may apply a diffusional thermal cooling method to send the aerosolized particles (or the droplets) into the saturated vapor chamber 1520, such that the aerosolized particles may absorb the vapor through heterogeneous nucleation. After the aerosolized particles leave the saturated vapor chamber 1520, the saturated vapor is rapidly cooled and condensed on the surfaces of the aerosolized particles, and thus the aerosolized particles can be transformed into the relatively large droplets. In an embodiment of the disclosure, supersaturation and condensation easily occur in the center of the chamber along a flow direction, e.g., in a region A, sheath fluids can be added to the inside of the saturated vapor chamber 1520, such that the aerosolized particles are concentrated and pass through the saturated vapor chamber 1520. Thereby, it can be ensured that most of the aerosolized particles can be vapor-encapsulated and condensed. The grown particles that undergo condensation may be concentrated by a nozzle (not shown); after that, the droplets sequentially pass through an optical sensor one by one and are then counted.

The solution mixing apparatus and the method for mixing particles in the solution provided in an embodiment of the disclosure allow the increase in the number of times of the solution flowing through the mixer, so as to compensate for the reduction of the mixing effects caused by the insufficient size of the mixer and further satisfy the requirements for miniaturizing the solution mixing apparatus and enhancing the mixing effects of the solution mixing apparatus. If, from another perspective, the solution mixing apparatus is integrated into a monitoring apparatus, the particles in a solution can then be monitored by said monitoring apparatus. First, the sampling element of the solution mixing apparatus is configured to extract a solution with a constant volume as well as dilute and mix the solution at a predetermined ratio, and the resultant solution acts as the sample solution. The aerosolization apparatus can aerosolize the sample solution into a plurality of aerosolized particles. The particle size classifier can classify the aerosolized particles whose sizes fall within a designated range, and the particle counter calculates the number of the classified aerosolized particles. If the solution does not require the pre-treatment, e.g., dilution and mixture, said sampling step and pre-treatment may be omitted; instead, the to-be-tested solution is introduced into the aerosolization apparatus to form the aerosolized particles, and subsequent steps may then be performed. As a result, the solution having the particles with different diameters can be accurately analyzed, so as to satisfy the requirement for automation and for online monitoring of particles in the solution.

It will be clear that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A system for monitoring particles in a solution, comprising:
    a solution mixing apparatus configured to extract a first solution with a fixed volume as well as dilute and mix the first solution at a predetermined ratio to form a sample solution, wherein the solution mixing apparatus comprises:
        a first tank having a first chamber and a first fluid inlet and placing the first solution;
        a sampling element connected to the first chamber;
        a flow control element connecting and communicating with the first chamber through the first fluid inlet, so as to control a volume of a second solution flowing into the first tank;
        a second tank having a second chamber; and
        a mixing assembly, comprising a mixer and two second conduits respectively connecting and communicating with two opposite ends of the mixer, wherein the two second conduits respectively connect and communicate with the first chamber and the second chamber; and
    an analysis equipment connected to the solution mixing apparatus, the analysis equipment comprising:
        an aerosolization apparatus configured to extract the sample solution and aerosolize the sample solution into a plurality of aerosol particles;
        a particle size classifier connected to the aerosolization apparatus and configured to receive the aerosolized particles and classify the aerosolized particles by sizes; and
        a particle counter connected to the particle size classifier and configured to receive these classified aerosolized particles and count the number of the classified aerosolized particles.

2. The system according to claim 1, wherein the first tank further comprises a first air-intake port and a first air-exhaust port, the first fluid inlet, the first air-intake port, and the first air-exhaust port connecting and communicating with the first chamber, the solution mixing apparatus further comprises:
    a first air-intake system and a first air-exhaust system respectively connecting and communicating with the first chamber through the first air-intake port and the first air-exhaust port; and
    a first conduit and a first switch valve arranged on the first conduit, the first tank further having a second fluid inlet, the second fluid inlet connecting and communicating with the first chamber, the second fluid inlet connecting and communicating with a pipeline through the first conduit.

3. The system according to claim 1, wherein the sampling element is a syringe pump, a peristaltic pump, or a sample loop with a pump.

4. The system according to claim 1, wherein the sampling element comprises an infusion valve and a sampling valve, the sampling valve connects and communicates with the first tank, the infusion valve connects and communicates with the sampling valve, the first solution is infused into the sampling valve through the infusion valve and infused into the first chamber from the sampling valve, and the sampling valve has a micro-dosing pipe for infusing the first solution with a predetermined volume into the first chamber.

5. The system according to claim 2, wherein the first air-intake system comprises:
   a first air-intake equipment;
   a first air-intake conduit, two opposite ends of the first air-intake conduit connecting and communicating with the first air-intake port and the first air-intake equipment, respectively; and
   a first air-intake valve arranged on the first air-intake conduit.

6. The system according to claim 2, wherein the first air-exhaust system comprises:
   a first air-exhaust equipment;
   a first air-exhaust conduit, two opposite ends of the first air-exhaust conduit connecting and communicating with the first air-exhaust port and the first air-exhaust equipment, respectively; and
   a first air-exhaust valve arranged on the first air-exhaust conduit.

7. The system according to claim 1, wherein the second tank further has a second air-intake port and a second air-exhaust port, the second air-intake port and the second air-exhaust port respectively connecting and communicating with the second chamber, the solution mixing apparatus further comprises:
   a second air-intake system and a second air-exhaust system respectively connecting and communicating with the second chamber through the second air-intake port and the second air-exhaust port.

8. The system according to claim 1, wherein the mixer is a static mixer and the mixing assembly further comprises:
   two second switch valves respectively arranged on the two second conduits;
   a drain conduit connecting and communicating with the second conduit between the first tank and the mixer; and
   a drain switch valve arranged on the drain conduit.

9. The system according to claim 1, further comprising:
   a connection conduit, two opposite ends of the connection conduit respectively connecting with the first chamber and the second chamber;
   two third ports valves arranged on the two opposite ends of the connection conduit;
   a drain conduit connecting and communicating with the connection conduit; and
   a drain switch valve arranged on the drain conduit.

10. The system according to claim 7, wherein the second air-intake system comprises:
    a second air-intake equipment;
    a second air-intake conduit, two opposite ends of the second air-intake conduit connecting with the second air-intake port and the second air-intake equipment, respectively; and
    a second air-intake valve arranged on the second air-intake conduit.

11. The system according to claim 7, wherein the second air-exhaust system comprises:
    a second air-exhaust equipment;
    a second air-exhaust conduit, two opposite ends of the second air-exhaust conduit connecting and communicating with the second air-exhaust port and the second air-exhaust equipment, respectively; and
    a second air-exhaust valve arranged on the second air-exhaust conduit.

12. The system according to claim 7, further comprising a controller controlling the sampling element, the flow control element, the first air-intake system, the first air-exhaust system, the second air-intake system, and the second air-exhaust system.

13. The system according to claim 7, wherein air driven by the first air-intake system, the first air-exhaust system, the second air-intake system, and the second air-exhaust system comprises compressed air, nitrogen, or an inert gas.

14. The system according to claim 1, wherein the aerosolization apparatus comprises:
    a sample solution guiding inlet connecting and communicating with the solution mixing apparatus;
    an aerosolized particle guiding outlet opposite to the sample solution guiding inlet;
    an aerosolization generator comprising:
       an aerosolized aperture located between the sample solution guiding inlet and the aerosolized particle guiding outlet;
       a high-pressure air guiding inlet connected to the aerosolized aperture;
       a heating element, the aerosolized aperture being arranged between the sample solution guiding inlet and the heating element; and
       a drying element, the aerosolized aperture being arranged between the sample solution guiding inlet and the drying element.

15. The system according to claim 14, wherein the heating element or the drying element is located in front of or in the rear of the aerosolized particle guiding outlet.

16. The system according to claim 1, wherein the particle size classifier comprises:
    an aerosolized particle guiding inlet connecting and communicating with the aerosolization apparatus;
    a particle size classification chamber connecting and communicating with the aerosolized particle guiding inlet;
    a neutralizer arranged between the aerosolized particle guiding inlet and the particle size classification chamber;
    an outlet of classified particles, the outlet connecting and communicating with the particle size classification chamber; and
    a surplus fluid outlet connecting and communicating with the particle size classification chamber.

17. The system according to claim 1, wherein the particle counter comprises:
    an aerosolized particle guiding inlet connecting and communicating with the particle size classifier;
    a saturated vapor chamber connecting and communicating with the aerosolized particle guiding inlet;
    a condenser connecting and communicating with the saturated vapor chamber, the saturated vapor chamber being located between the aerosolized particle guiding inlet and the condenser; and
    a light source and light detection module located in the rear of the condenser.

18. A method for monitoring particles in a solution by using the system recited in claim 1, the method comprising:
    diluting and mixing a solution by a solution mixing apparatus
    aerosolizing the sample solution into the aerosolized particles by the aerosolization apparatus;
    classifying the aerosolized particles whose sizes fall within a designated range by the particle size classifier; and counting the number of the classified aerosolized particles by the particle counter.

19. The method according to claim 18, further comprising:
introducing the first solution into the solution mixing apparatus and extracting the first solution with the fixed volume by the solution mixing apparatus; and
diluting and mixing the first solution with second solution at a predetermined ratio by the solution mixing apparatus to form the sample solution.

* * * * *